(12) United States Patent
Colgin et al.

(10) Patent No.: US 7,670,789 B2
(45) Date of Patent: Mar. 2, 2010

(54) METHODS AND DEVICES FOR DIAGNOSIS OF APPENDICITIS

(75) Inventors: Mark A. Colgin, Castle Rock, CO (US); John F. Bealer, Englewood, CO (US); Richard G. Donnelly, Fort Collins, CO (US); Diane Newman, Castle Rock, CO (US)

(73) Assignee: AspenBio Pharma, Inc., Castle Rock, CO (US)

( * ) Notice: Subject to any disclaimer, the term of this patent is extended or adjusted under 35 U.S.C. 154(b) by 0 days.

(21) Appl. No.: 12/369,640

(22) Filed: Feb. 11, 2009

(65) Prior Publication Data

US 2009/0155813 A1 Jun. 18, 2009

Related U.S. Application Data

(62) Division of application No. 11/189,120, filed on Jul. 25, 2005, now Pat. No. 7,501,256.

(60) Provisional application No. 60/590,631, filed on Jul. 23, 2004.

(51) Int. Cl.
G01N 33/53 (2006.01)
G01N 33/567 (2006.01)

(52) U.S. Cl. .................... 435/7.1; 435/7.2; 435/810; 436/518

(58) Field of Classification Search .................... None
See application file for complete search history.

(56) References Cited

U.S. PATENT DOCUMENTS

| | | | |
|---|---|---|---|
| 4,493,795 A | 1/1985 | Nester, Jr. et al. |
| 4,833,074 A | 5/1989 | Fagerhol et al. |
| 5,055,389 A | 10/1991 | Bar-or et al. |
| 5,350,687 A | 9/1994 | Odink et al. |
| 5,455,160 A | 10/1995 | Fagerhol et al. |
| 5,470,750 A | 11/1995 | Bar-Or |
| 5,552,295 A | 9/1996 | Stanker et al. |
| 5,702,920 A | 12/1997 | Odink et al. |
| 6,451,550 B1 | 9/2002 | Eckersall |
| 6,749,565 B2 | 6/2004 | Chundner |
| 2003/0224452 A1 | 12/2003 | Colgin et al. |
| 2004/0121343 A1 | 6/2004 | Buechler et al. |
| 2004/0175754 A1 | 9/2004 | Bar-Or et al. |
| 2004/0241775 A1 | 12/2004 | Romero et al. |
| 2005/0095249 A1 | 5/2005 | Hanash |
| 2006/0024719 A1 | 2/2006 | Colgin et al. |
| 2007/0249003 A1 | 10/2007 | Colgin et al. |

FOREIGN PATENT DOCUMENTS

| | | |
|---|---|---|
| EP | 0263072 | 4/1988 |
| EP | 0 428 080 | 5/1991 |
| EP | 058201 | 3/1994 |
| JP | 9-188698 | 7/1997 |
| JP | 2001-512314 | 8/2001 |
| JP | 2003-517579 | 5/2003 |
| JP | 2006-177679 | 7/2006 |
| JP | 2006-517286 | 7/2006 |
| JP | 2006-256140 | 11/2006 |
| WO | WO 98/35985 | 8/1998 |
| WO | WO 00/26668 | 5/2000 |
| WO | WO 03/069349 | 8/2003 |
| WO | WO 2004/032711 | 4/2004 |
| WO | WO 2004/057341 | 7/2004 |
| WO | WO 2004/059293 | 7/2004 |
| WO | WO2006/012588 | 2/2006 |
| WO | WO 2008/097773 | 8/2008 |

OTHER PUBLICATIONS

Aadland et al. (2002) "Faecal Calprotectin: A Marker of Inflammation Throughout the Intestinal Tract," *Eur. J. Gasroenterol Hepatol.* 14:1823-825.

Ahlquist et al. (1996) "Stool Markers for Colorectal Screening: Future Considerations," *Dig. Dis.* 14(3):132-144.

Alic, M. (1999) "Is Fecal Calprotectin the Next Standard in Inflammatory Bowel Disease Activity Tests," (letter) *Am. J. Gastroenterol.* 94(11):3370-3371.

Arnott et al. (2002) "Review Article: Is Clinical Remission the Optimum Therapeutic Goal in the Treatment of Crohn's Disease," *Aliment Pharmacol. Ther.* 16:857-867.

Arredouani et al. (2005) "Haptoglobin Dampnes Endotoxin-Induced Inflammatory Effects Both In Vitro and In Vivo," *Immunology* 114(2):263-271.

Avrameas et al. (1978) "Coupling of Enzymes to Antibodies and Antigens," *Scand. J. Immunol.* 8(7):7-23.

Barcia et al. (Dec. 2002) "Neutrophil Count in Normal Appendix and Early Appendicitis: Diagonstic Index of Real Acute Inflammation," *Ann. Diag. Path.* 6(6):352-356.

Berger et al. (1997) "Time-Scale of Interleukin-6, Myeloid Related proteins (MRP), C Reactive Protein (CRP, and Endotoxin Plasma Levels During the Postoperative Acute Phase Reaction," *Shock* 7(6):422-426.

Berntzen et al. (1991) "Calprotectin (The L1 Protein) During Surgery in Patients with Rheumatoid Arthritis," *Scand. J. Clin. Lab. Invest.* 51(7):643-650.

(Continued)

*Primary Examiner*—Prema Mertz
(74) *Attorney, Agent, or Firm*—Greenlee, Winner and Sullivan, P.C.

(57) ABSTRACT

A method is provided for diagnosing appendicitis in a patient that includes identifying at least one symptom of appendicitis in the patient and identifying the presence of at least one molecule differentially associated with appendicitis in a fluid or tissue sample of said patient. MRP-8/14 and haptoglobin are examples of molecules differentially associated with appendicitis. Devices and kits for performing the appendicitis assays of this invention are also provided. In one embodiment, the device is in a flow-through immunoassay format for testing blood samples. Further, methods for screening for molecules differentially associated with appendicitis are provided that include the use of samples from patients being operated on for suspected appendicitis.

12 Claims, 9 Drawing Sheets

OTHER PUBLICATIONS

Berntzen et al. (1991) "The L1 Protein as a New Indicator of Inflammatory Activity in Patients with Juvenile Rheumatoid Arthritis," *J. Rheumatol.* 18(1):133-138.

Berntzen et al. (1989) "A Longitudinal Study of the Leukocyte Protein L1 as an Indicator of Disease Activity in Patients with Rheumatoid Arthritis," *J. Pheumatol.* 16(11):1416-1420.

Berntzen et al. (1988) "The Major Leukocyte Protein L1 as an Indicator of Inflammatory Joint Disease," *Scand. J. Rheumatol.* Supp 76:251-256.

Berntzen et al. (1991) "The Leukocyte Protein L1 in Plasma and ynovial Fluid from Patients with Rheumatoid Arthritis and Osteoarthritis," *Scand J. Rheumatol.* 20(2):74-82.

Berstad et al. (2000) "Relationship Between Intestinal Permeability and Calprotectin in Gut Lavage Fluid," *Scand J. Gastroenterol.* 35(1):64-69.

Bhardwaj, R.S. (1992) "The Calcium-Binding Proteins MRP8 and MRP14 form a Membrane-Associated Heterodimer in a Subset of Monocytes/Macrophages Present in Acute but Absent in Chronic Inflammatory Lesions," *Eur. J. Immunol.* 22(7):1891-1897.

Birchley, D. (2006) "Patients with Clinical Acute Appendicitis Should Have Pre-Operative Full Blood Count and C-Reactive Protein Assays," *Ann. R. Coll. Surg. Engl.* 88:27-32.

Bjarnason et al. (2001) "Fecal Calprotectin: A Significant Step in the Noninvasive Assessment of Intestinal Inflammation," *J. Pediat. Gastroent.Nutr.* 33:11-13.

Bjerke et al. (1993) "Distribution of Macrophages and Granulocytes Expressing L1 Protein (Calprotectin) in Human Peyer's Patches Compared with Normal Ileal Lamina Propria and Mesenteric Lymph Nodes," *Gut* 34(10):1357-1363.

Bogumil et al. (1998) "Serum Levels of Macrophage-Derived Protein MRP8/14 are Elevated in Active Multiple Sclrosis," *Neurosci. Lett.* 247(2-3):195-197.

Bonaldo et al. (1996) "Normalization and Subtraction: Two Approaches to facilitate Gene Discovery," *Genmome Res.* 6:791-806.

Brandtzaeg et al. (1987) "Distribution of a Formalin-Resistant Myelomonocytic Antigen (I1) in Human Tissues. I. Comparison with Other Leukocyte Markers by Paired Immunofluorescence and Immunoenzyme Staining," *Am. J. CLin. Pathol.* 87(6):681-699.

Brandtzaeg et al. (1987) "Distribution of a Formalin-Resistant Myelomonocytic Antigen (I1) in Human Tissues. II. Normal and Aberrant Occurence in Various Epithelia," *Am. J. Clin. Pathol.* 87(6):700-707.

Brantzaeg et al. (1992) "The Leucocyte Protein L1 (Calprotectin): Usefulness as an Immunohistochemical Marker Antigen and Putative Biological Function," *Histopathol.* 21(2):191-196.

Brun et al. (1994) "Sjögren's Syndrom in Inflammatory Rheumatic Disease: Analysis of the Leukocyte Protein Calprotectin in Plasma and Saliva," *Scand. J. Rheumatol.* 23(3):114-118.

Brun et al. (1992) "Calprotectin in Patients with Rheumatoid Arthiritis: Relation to Clinical and Laborotory Variables of Disease Activity," *J. Rheumatol.* 19(6):859-862.

Brydon et al. (2001) "Faecal Calprotectin Levels and Colorectal Neoplasia," *Gut* 48(4):579-580.

Bunn et al. (2001) "Fecal Calprotecin as a Measure of Disease Activity in Childhood Inflammatory Bowel Disease," *J. Pediat. Gastroenterol. Nutr.* 32(2):171-177.

Bunn et al. (2001) "Fecal Calprotectin: Validation as a Noninvasive Measure of Bowel Inflammation in Childhood Inflammatory Bowel Disease," *J. Pediat. Gastroenterol. Nutr.* 33(1):14-22.

Burkhardt et al. (2001) "An Increase in Myeloid-Related Protein Serum Levels Precedes Acute Renal Allograft Rejection," *J. Am. Soc. Nephrol.* 12:1947-1957.

Cell Sciences. Human Calprotectin ELISA Kit. 2006. IN: Cell Sciences Inc. Datasheet, http://www.cellsciences.com/content/p-detail.asp?rowid=8403.

Cell Sciences. Anti-Human S100A8/A9 (MRP-8/MRP-14), Calprotectin, Clone 27E10, Monoclonal Antibody. 2006, IN: Cell Sciences Inc. Datasheet, http://www.cellsciences.com/content/p-detail.asp?rowid=7581.

Clark et al. (1990) "Calgranulin Expression and Association with the Keratinocyte Cytoskeleton," *J. Pathol.* 160(1):25-30.

Cunliffe, R.N. (2003) "α-Defensins in the Gastrointestinal Tract," *Mol. lmmunol.* 40:463-467.

Cunliffe et al. (2004) "Expression and Regulation of Antimicrobial Peptides in the Gastrointestinal Tract," *J. Leuk. Biol.* 75:49-58.

Dale et al. (1985) "Distribution of a New Myelomonocytic Antigen (L1) in Human Peripheral Blood Leulocytes. Immunofluorescence and Immunoperoxidase Staining Features in Caomparison with Lysozyme and Lactoferrin," *Am. J. Clin. Pathol.* 84(1):24-34.

Dale et al. (1989) "Expression of the Epithelial L1 Antigen as an Immunohistochemical Marker or Squamous Cell Carcinoma of the Lung," *Histopathology* 14(5):493-502.

Dale, I. (1990) "Plasma Levels of the Calcium-Binding L1 Leukocyte Protein: Standardization of Blood Collection and Evaluation of Reference Intervals in Healthy Controls," *Scand. J. Clin. Lab. Invest.* 50(8):837-841.

Deichmann et al. (2001) "The Protein Phosphatase 2A Subunit Bg Gene is Identified to be Differentially Expressed in Malignant Melanomas by Subtractive Suppression Hybridization," *Melanoma Res.* 11(6):577-585.

DeLuca (1982) "Immunofluorescence Analysis," In; *Antibody as a Tool*, Marchalonis et al. Eds., John Wiley and Sons, Ltd., pp. 189-231.

Dorbryszycka, W. (1997) "Biological Functions of Haptoglobin—New Pieces to an Old Puzzle," *Eur. J. Clin. Chem. Clin. Biochem.* 35(9):647-654.

Eversole et al. (1993) "Keratinocyte Expression of Calprotectin in Oral Inflammatory Mucosal Disease," *J. Oral.. Pathol. Med.* 22(7):303-307.

Eversole et al. (1992) "The Distribution of the Antimicrobial Protein, Calprotectin, in Normal Oral Keratinocytes," *Arch. Oral. Biol.* 37(11):963-968.

Fagerhol et al. (1990) "Calprotectin (The L1 Leukocyte Protein)," In; *Stimulus Response Coupling. The Role of Intracellular Calcium-Binding Proteins*, Smith et al. Eds., CRC Press, Boca Raton, Fl., USA, pp. 187-210.

Flagerhol, M.K. (2000) "Calprotectin, a Faecal Marker of Organic Gastrointestinal Abnormality," *Lancet* 356(9244):1783-1784.

Flum et al. (2001) "Has Misdiagnosis of Appendicitis Decreased over Time? A Population-Based Analysis," *JAMA* 286(14):1748-1753.

Foell et al. (2003) "Neutrophil Derived Human S100A12 (EN-RAGE) is Strongly Expressed During Chronic Active Inflammatory Bowel Disease," *Gut* 52:847-853.

Fosse et al. (1994) "Reduced Complement and Granulocyte Activation with Heparin-Coated Cardiopulmonary Bypass," *Ann. Thoracic Surg.* 58(2):472-477.

Frosch et al. (2000) "Myloid-Related Proteins 8 and 14 are Specifically Secreted During Interaction of Phagocytes and Activated Endothelium and are Useful Markers for Monitoring Disease Activity in Pauciarticular-Onset Juvenile Rheumatoid Arthritis," *Arthritis Rheum.* 43:628-637.

Gabrielsen et al. (1986) "Epidermal and Dermal Distribution of a Myelomonocytic Antigen (L1) Shared by Epithilial Cells in Various Inflammatory Skin Disease," *J. Am Acad. Dermatol.* 15(2 pt 1):173-179.

Gabrielsen et al. (1988) "Epithelial Distribution of a Myelomonocytic Antigen L1 in Relation to Cutaneous Melignancies and Melanocytic Naevi," *Br. J. Dermatol.* 118(1):59-67.

Galfre et al. (1981) "Preparation of Monoclonal Antibodies: Strategies and Procedures," *Meth. Enzymol.* 73:3-46.

Garred et al. (1993) "Calprotectin and Complement Activation During Major Operations With or Without Cardiopulmonary Bypass," *Ann. Thoracic Surg.* 55(3):694-699.

Gasché, C. (2005) "Laboratory Tests—What do They Tell Us," Falk Symposium Abstract, Jun. 17-18, 2005, Munich, Germany.

Gaya et al. (2002) "Faecal Calprotectin: A Bright Future for Assessing Disease Activity in Crohn's Disease," *Q. J. Med.* 95:557-558.

GenBank Accession No. NP005134 , Oct. 23, 2005.

GenBank Accession No. P06702 , Sep. 13, 2005.

Giampalmo et al. (1983) "Enzymatic Activation of Lymphoid Population Following Inflammatory Reactions in the Human Appendix," *Z Mikrosk Anat Forsch* 97(5):785-796 Abstract Only.

Gilbert et al. (1996) "Fecal Marker Variability in Colorectal Cancer: Calprotectin Versus Hemoglobin," *Scand. J. Gastroenterol.* 31(10):1001-1005.

Golden et al. (1996) "Calprotectin as a Marker of Inflammation in Cystic Fibrosis," *Arch. Dis. Childhood* 74(2):136-139.

Haga et al. (1993) "Calprotectin in Patients with Systemic Lupus Erythematosus: Relation to Clinical and Laboratory Parameters of Disease Activity," *Lupus* 2(1):47-50.

Haidekker et al. (2002) "A Novel Approach to Blood Plasma Viscosity Mesurement Using Fluorescent Molecular Rotors," *Am. J. Physiol. Heart Circ. Physio.* 282:H1609-1614.

Hammer et al. (1995) "A Longitudinal Study of Calprotectin as an Inflammatory Marker in Patients with Reactive Arthritis," *Clin. Exp. Rheumatol.* 13(1):59-64.

Hanai et al. (2003) "Clinical Significance of Faecal Calprotectin Levels in Patients with Ulcerative Colitis," *Nippon Shokakibyo Gakkai Zasshi* 100:21-27.

Harkness, J. (1963) "A New Method for the Measurement of Plasma Viscosity," *Lancet* 2:280-281.

Hessian et al. (2001) "The Heterodimeric Complex of MRP-8 (S100A8) and MRP-14 (S100A9): Antibody Recognition, Epitope Definition and the Implications for Structure," *Eur. J. Biochem.* 268:353-363.

Hessian et al. (Feb. 1993) "MRP-8 and MRP-14, Two Abundant Ca2+-Binding Proteins of Neutrophils and Monocytes," *J. Leuk Biol.* 53:197-204.

Hetland et al. (1992) "Levels of Calprotectin (leukocyte L1 Protein) During Apheresis," *Scand. J. CLin. Lab. Invest.* 52(6):479-482.

Homann et al. (1995) "Plasma Calprotectin: A New Prognostic Marker of Survival in Alchohol-Induced Cirrhosis," *Hapatol.* 21(4):979-985.

Hsieh et al. (2004) "S100 Protein Translocation in Response to Extracellular S100 is Mediated by Receptor for Advanced Glycation Endproducts in Humna Endothelial Cells," *Biochm. Biophys. Res. Commun.* 316:949-959.

Hycult Biotechnology b.v., "Monoclonal Antibody to Human S100A8/A9 (MRP-8/MRP-14)," Calprotectin Clone 27E10 Information Sheet, Catalog No. HM2156, (2005).

Hycult Biotechnology b.v., "ELISA Test Kit Human Calprotectin," Information Sheet, Catalog No. HK325, (2005).

Ikemoto et al. (2003) "New ELISA System for Myeloid-Related Protein Complex (MRP8/14) and its Clinical Significance as a Sensitive Marker for Inflammatory Responses Associated with Transplant Rejection," *Clin. Chem.* 49:594-600.

Johne et al. (1997) "Functional and Clinical Aspects of the Myelomonocyte Protein Calprotectin," *Mol. Pathol.* 50(3):113-123.

Johne et al. (2001) "A New Fecal Calprotectin Test for Colorectal Neoplasia. Clinical Results and Comparison with Previous Method," *Scand. J. Gastroenterol.* 36(3):291-296.

Katnik et al. (1989) "Monoclonal ANtibodes Against Human Haptoglobin," *Hybridoma* 8(5):551-560.

Kelly et al. (1991) "Morphological Evidence for Calcium-Dependent Association of Calgranulin with the Epdermal Cytoskeleton in Inflammatory Dermatoses," *Br. J. Dermatol.* 124(5):403-409.

Kelly et al. (1989) "Calgranulin Expression in Inflammatory Dermatoses," *J. Pathol.* 159(1):17-21.

Kerkhoff et al. (1998) "Novel Insights into Structure and Function of MRP8 (S100A8) and MRP14 (S100A9)," *Biochim.I Biophys. Acta* 1448(2):200-211.

Kjeldsen-Kragh et al. (1995) "Changes in Laboratory Variable in Rheumatoid Arthritis Patients During a Trial of Fasting and One-Year Vegetarian Diet," *Scand. J. Rheumatol.* 24(2):85-93.

Koike et al. (1998) "Intracellular Localization of Migration Inhibitory Factor-Related Protein (MRP) and Detection of Cell Surface MRP Binding Sites on Human Leukemia Cell Lines," *J. Biochem.* 123(6):1079-1087.

Kristinsson et al. (1998) "Fecal Excretion of Calprotectin Concentration in Patients with Colorectal Carcinoma," *Dos. Colon Rectum* 41(3):316-321.

Kristinsson et al. (2001) "Fecal Ecretion of Calprotectin in Colorectal Cancer; Relationship to Tumor Characteristics," *Scand. J. Gastroenterol.* 36(2):202-207.

Kronborg et al. (2000) "Faecal Calprotectin Levels in a High Risk Population for Colorectal Neoplasia," *Gut* 46(6):795-800.

Kumar et al. (2001) "Dimeric S100A8 in Human Neutrophils is Diminished After Phagocytosis," *J. Leukoc. Biol.* 70(1):59-64.

Limburg et al. (2000) "Fecal Calprotectin Levels Predict Colorectal Inflammation Among Patients with hronic Diarrhea Referred for Colonoscopy," *Am. J. Gastroenterol* 95(10):2831-2837.

Longbottom et al. (1992) "Subunit Structure of Calgranulins A and B Obtained from Sputum, Plasma, Granulocytes and Cultures Epithelial Cells," *Biochim. Biophys. Acta* 1120(2):215-222.

Lugering et al. (1995) "The Myeloic Related Protein MRP8/14 (27E10 Antigen)-Usefulness as a Potential Marker for DIsese Activity in Ulcerative Colitis and Putative Biological Function," *Eur. J. Clin. Invest.* 25(9):659-664.

Maruniak et al. (1987) "Acute Phase Reactants in Inflammatory Conditions of the Colon Relationship with Nerve Hypertrophy," *Fed. Proc.* 46(3):986, Abstract No. 3900.

Meling et al. (1996) "Faecal Calprotectin Shedding After Short-Term Treatment with Non-Steroidal Anti-Inflammatory Drugs," *Scand. J. J. Gastroenterology* 31(4):339-34.

Moen et al. (1994) "Roller and Centrifugal Pumps Compared in Vitro with Regard to Haemolysis, Granulocyte and Complement Activation," *Perfusion* 9(2):109-117.

Muller et al. (1994) "Elevated Serum Calprotectin Levels in HIV-Infected Patients: The Calprotectin Response During ZDV Treatment is Associated with Clinical Events," *J. Acq. Immun. Def. Syndr.* 7(9):931-939.

Neary, W. (2001) Misdiagnosis of Appendicitis Continues Despite New Tools, Press Release from University of Washington.

Ng et al. (Feb. 2002) "Clinical Analysis of the Related Factors in Acute Appendicitis," *Yale J. Biol. Med.* 75:41-45.

Olafsdottir et al. (2002) "Faecal Calprotectin in Infants with Infantile Colic, Healthy Infants, Children with Inflammatory Bowel Disease, Children with Recurrent Abdominal Pain and Healthy Children," *Acta Paediatr.* 91:45-50.

Pekna et al. (194) "Biocompatibility of Heparin-Coated Circuits Used in Cardiopulmonary By[ass," *Scand. J. Thorasc. Cardiovasc. Surg.* 28(1):5-11, (1994).

Power et al. (2005) "Raised Faecal Calprotectin Levels in Patients Presenting with Right Iliac Fossa Pain Warrant Mandatory Laparoscopy: A Non-Invasive Predictor of Acute Appendicitis," *Thieme Connect, Endoscopyl* 37:DOI:10.1055/2-2005-868524.

Power et al. (2004) "Raised Faecal Calprotecting Levels in Patients Presenting With Right Iliac Fossa Pain Warrant Mandatory Laparoscopy: A Non-Invasive Predictor of Acture Appendicitis," Irish Society of Gastoenterology Winter Meeting Program, Oral Presentation.

Que et al. (2004) "Myeloid-Related Protein (MRP)8/14 (Calprotectin) and its Subunits MRP8 and MRP14 in Plaque-Induced Early Gingival Inflammation," *J. Clin. Peridon.* 31(11):978-984.

Riviera-Chavez et al. (Mar. 2003) "Reginal and Systemic Cytokine Responses to Acute Inflammation of the Veriform Appendix," *Ann. Surg.* 237(3):408-416.

Robinson et al. (2002) "The S100 Family Heterodimer, MRP8/14, Binds with High Affinity to Heparin and Heparan Sulfate Glycosaminoglycans on Endothelial Cells," *J. Biol. Chem.* 277:3658-3665.

Rodwell et al. (1984) "Linker Technology: Antibody-Mediated Delivery Systems," *Biotech.* 3:889-894.

Roseth et al. (Oct. 2004) "Normalization of Faecal Calprotectin: A Predictor of Mucosal Healing in Patients with Inflammatory Bowel Disease," *Scand. J. Gastroenterol.* 39(10):1017-1020.

Roseth et al. (1992) "Assessment of the neutrophil Dominating Protein Calprotectin in Feces. A Methodologic Study," *Scand. J. Gastroenterol.* 27(9):793-798.

Roseth et al. (1993) "Faecal Calprotectin: A Novel Test for the Diagnosis of Colorectal Cancer," *Scand J. Gastroenterol.* 28(12):1073-1076.

Roseth et al. (1997) "Assessment of Disease Activity in Ulcerative Colitis by Faecal Calprotectin, A Novel Granulocyte Marker Protein," *Digestion* 58(2):176-180.

Roseth et al. (1999) "Correlation Between Feacal Excretion of indium-111-labelled Granulocytes and Calprotectin, a Granulocyte Marker Protein, in Patients with Inflammatory Bowel Disease," *Scand. J. Gastroenterol.* 34(1):50-54.

Roth et al. "Expression of the Calcium-Binding Proteins MRP8 and MRP14 in Monocytes is Regulated by a Calcium-Induced Suppressor Mechanism," *Biochem. J.* 301:655-660, (1994).

Rychman et al. (2003) "Proinflammatory Activities of S100: Proteins S100A8, S100A9, and S100A8/A9 Induce Neutrophil Chemotaxis and Adhesion," *J. Immunol.* 170:3233-3242.

Rypins et al. (2002) "$^{99m}$Tc Anti-CD 15 Monoclonal Antibody (LeuTech) Imaging Improves Diagnostic Accuracy and Clinical Management in Patients with Equivocal Presentation of Appendicitis," *Ann. Surg.* 235(2):232-239.

Sack et al. (2006) "Diagnostic Value of Blood Inflammatory Markers for Detection of Acute Appendicitis in Children," *BMC Surg.* 6:15.

Saintigny et al. (1992) "Differential Expression of Calgranulin A and B in Various Epithelial Cell Lines and Reconstructed Epidermis," *J. Invest. Dermatol.* 99(5):639-644.

Sander et al. (1984) "Plasma Levels of the Leucocyte L1 Protein in Febrile Conditions: Relation to Aetiology, Number of Leucocytes in Blood, Blood Sedimentation Reaction and C-Reactive Protein," *Scand. J. Clin. Lab. Invest.* 44(4):357-362.

Semb et al. (1991) "Cardiac Surgery and Distribution of the Leukocyte L1 Protein-Calprotectin," *Eur. J. Cardio-Thoracic Surg.* 5(7):363-367.

Shanahan, F. (2001) "Inflammatory Bowel Disease Immunodiagnostics, Immunotherapeutics, andd Ecotherapeutics," *Gastroenterol.* 120:622-635.

Stockley et al. (1984) "Relationship of Neutrophil Cytoplasmic Protein (I1) to Acute and Chronic Lung Disease," *Scand. J. CLin. Lab. Invest.* 44(7):629-634.

Striz et al. (2004) "Calprotectin—A Pleiotropic Molecule in Acute and Chronic Inflammation," *Physiol. Res.* 53:245-253.

Supplementary Partial European Search Report, Corresponding to European Application No. 05 77 5574, Completed on Jan. 14, 2008.

Thomas et al. (2000) "Assessment of Ileal Pouch Inflammation by Single-Stool Calprotectin Assay," *Dis. Colon Rectum* 43(2):214-220.

Tibble et al. (2000) "A Simple Method for Assessing Intestinal Inflammation in Crohn's Disease," *Gut* 47(4):506-513.

Tibble et al. (2001) "Faecal Calprotectin and aecal Occult Blood Tests in the Diagnosis of Colorectal Carcinoma and Adenoma," *Gut* 49:402-408.

Tibble et al. "Non-Invasive Investigation of Flammatory Bowel Disease," *World J. Gastroenterol.* 7(4):460-465, (2001).

Tibble et al. "Fecal Calprotectin as an Index of Intestinal Inflammation," *Drugs of Today* 37(2):85-96, (2001).

Tibble et al. (2001) "Markers of Intestinal Inflammation and Predictors of Clinical Relapse in Patients with Quiescent IBD," *Medscape Gastroenterol.* 3(2):1-4.

Tibble et al. (2000) "Surrogate Markers of Intestinal Inflammation are Predictive of Relapse in Patients with Inflammatory Bowel Disease," *Gastroentology* 119(1):15-22.

Tibble et al. (1999) "High Prevalence of NSAID Enteropathy as Shown by a Simple Faecal Test," *Gut* 45(3):362-363.

Ton et al. (2000) "Improved Assay for Fecal Calprotectin," *Clinica Chimica Acta* 292(1-2):41-54.

Tungekar et al. (1991) "The L1 Antigen and Squamous Metaplasia in the Bladder," *Histopathol* 19(3):245-250.

Waraich et al. (Mar. 1997) "The Accessory Cell Populations in Ulcerative Colitis: A Comparison Between the Colon and Appendix in Colitis and Acute Appendicitis," *Hum. Pathol.* 28(3):297-303 Abstract Only.

Webpage information from internet at http://www.fda.gov/cder/drug/advisory/technetium99.htm, source material indicated as from Dec. 19, 2005.

Webpage information from Internet at http://www.palatin.com/neutrospecstatement.asp and at http://www.palatin.com/news/news.asp?ID=134 and , source material indicated as from Dec. 19, 2005.

Wehkamp et al. (2005) "Human Defensins in Crohn's Disease. A Molecular Link to Mucosal Barrier Dysfunction," *Chem. Immunol. Allergy* 86:42-54.

Wilkinson et al. (1988) "Expression Pattern of Two Related Cystic Fibrosis-Associated Calcium Binding Proteins in Normal and Abnormal Tissues," *J. Cell. Sci.* 91(2):221-230.

Yang et al. (2006) "Laboratory Tests in Patients with Acute Appendicitis," *ANZ J. Surg.* 76:71-74.

Ye et al. (2003) "Haptoglobin-Alpha as PotentialSerum Biomarker in Ovarian Cancer: Identification asnCharacterization Using Proteomic Profiling and Mass Spectometry," *Clin Cancer Res.* 9(8):2904-2911.

Yerly et al. (1990) "Development of a Haptoglobin ELISA. Its Use as an Indicator for Malaria," *Acta Trop.* 47(4):237-244.

Yildirim et al. (2006) "The Role of Serum Inflammatory Markers in Acute Appendicitis and Their Success in Preventing Negative Laparotomy," *J. Invest. Surg.* 19:345-352.

Yoon et al. (Dec. 2002) "Human Cytokine Levels in Nonperforated Versus Perforated Appendicitis: Milecular Serum Markers for Extent of Disease," *Am. Surg.* 68(12):1033-1037.

Yui et al., Biol Pharm Bull. Jun. 2003;26(6):753-760.

Zwaldo et al. (1986) "A Monoclonal Antibody to a Subset of Human Monocytes Found Only in the Peripheral Blood and Inflammatory Tissues," *J. lmmunol.* 137(2):512-518.

Lagasse et al. (1988) "Cloning and Expression of Two Human Genes Encoding Calcium-Binding Protein that are Regulated during Myeloid Differentiation," Molecular Cellular Biology, 8(6): 2402-2410.

Maeda et al. (1985) "Nucleotide Sequence of the Haptoglobin and Haptoglobin-related Gene Pair," The Journal of Biological Chemistry, 260(11): 6698-6709.

N. Lugering, et al. (1995), "Serum 27E10 antigen: a new potential marker for staging HIV disease," Clin. Exp. lmmunol. 101:249-253.

English translation of Japanese Official Action for corresponding Japanese Patent Application No. 2007-522830, dated Sep. 29, 2009 (mailed Oct. 1, 2009).

English translation of Japanese Official Action for corresponding Japanese Patent Application No. 2009-153020, dated Nov. 16, 2009 (mailed Nov. 18, 2009).

SEQUENCE LISTING

<160> NUMBER OF SEQ ID NOS: 6

<210> SEQ ID NO 1
<211> LENGTH: 15
<212> TYPE: PRT
<213> ORGANISM: Artificial sequence
<220> FEATURE:
<223> OTHER INFORMATION: Synthetic peptide

<400> SEQUENCE: 1

Asn Ile Glu Thr Ile Ile Asn Thr Phe His Gln Tyr Ser Val Lys
1               5                   10                  15

<210> SEQ ID NO 2
<211> LENGTH: 17
<212> TYPE: PRT
<213> ORGANISM: Artificial sequence
<220> FEATURE:
<223> OTHER INFORMATION: Synthetic peptide

<400> SEQUENCE: 2

Leu Gly His Pro Asp Thr Leu Asn Gln Gly Glu Phe Lys Glu Leu Val
1               5                   10                  15

Arg

<210> SEQ ID NO 3
<211> LENGTH: 114
<212> TYPE: PRT
<213> ORGANISM: Homo sapiens

<400> SEQUENCE: 3

Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
            20                  25                  30

Asn Gln Gly Glu Phe Lys Glu Leu Val Arg Lys Asp Leu Gln Asn Phe
        35                  40                  45

Leu Lys Lys Glu Asn Lys Asn Glu Lys Val Ile Glu His Ile Met Glu
    50                  55                  60

Asp Leu Asp Thr Asn Ala Asp Lys Gln Leu Ser Phe Glu Glu Phe Ile
65                  70                  75                  80

Met Leu Met Ala Arg Leu Thr Trp Ala Ser His Glu Lys Met His Glu
                85                  90                  95

Gly Asp Glu Gly Pro Gly His His Lys Pro Gly Leu Gly Glu Gly
            100                 105                 110

Thr Pro

<210> SEQ ID NO 4
<211> LENGTH: 18
<212> TYPE: PRT
<213> ORGANISM: Artificial sequence
<220> FEATURE:
<223> OTHER INFORMATION: Synthetic peptide

<400> SEQUENCE: 4

Thr Glu Gly Asp Gly Val Tyr Thr Leu Asn Asn Glu Lys Gln Trp Ile
1               5                   10                  15

Asn Lys

```
<210> SEQ ID NO 5
<211> LENGTH: 31
<212> TYPE: PRT
<213> ORGANISM: Artificial sequence
<220> FEATURE:
<223> OTHER INFORMATION: Synthetic peptide

<400> SEQUENCE: 5

Ala Val Gly Asp Lys Leu Pro Glu Cys Glu Ala Asp Asp Gly Cys Pro
1               5                   10                  15

Lys Pro Pro Glu Ile Ala His Gly Tyr Val Glu His Ser Val Arg
            20                  25                  30

<210> SEQ ID NO 6
<211> LENGTH: 406
<212> TYPE: PRT
<213> ORGANISM: Homo sapiens

<400> SEQUENCE: 6

Met Ser Ala Leu Gly Ala Val Ile Ala Leu Leu Leu Trp Gly Gln Leu
1               5                   10                  15

Phe Ala Val Asp Ser Gly Asn Asp Val Thr Asp Ile Ala Asp Asp Gly
            20                  25                  30

Cys Pro Lys Pro Pro Glu Ile Ala His Gly Tyr Val Glu His Ser Val
        35                  40                  45

Arg Tyr Gln Cys Lys Asn Tyr Tyr Lys Leu Arg Thr Glu Gly Asp Gly
    50                  55                  60

Val Tyr Thr Leu Asn Asp Lys Lys Gln Trp Ile Asn Lys Ala Val Gly
65                  70                  75                  80

Asp Lys Leu Pro Glu Cys Glu Ala Asp Asp Gly Cys Pro Lys Pro Pro
                85                  90                  95

Glu Ile Ala His Gly Tyr Val Glu His Ser Val Arg Tyr Gln Cys Lys
            100                 105                 110

Asn Tyr Tyr Lys Leu Arg Thr Glu Gly Asp Gly Val Tyr Thr Leu Asn
        115                 120                 125

Asn Glu Lys Gln Trp Ile Asn Lys Ala Val Gly Asp Lys Leu Pro Glu
    130                 135                 140

Cys Glu Ala Val Cys Gly Lys Pro Lys Asn Pro Ala Asn Pro Val Gln
145                 150                 155                 160

Arg Ile Leu Gly Gly His Leu Asp Ala Lys Gly Ser Phe Pro Trp Gln
                165                 170                 175

Ala Lys Met Val Ser His His Asn Leu Thr Thr Gly Ala Thr Leu Ile
            180                 185                 190

Asn Glu Gln Trp Leu Leu Thr Thr Ala Lys Asn Leu Phe Leu Asn His
        195                 200                 205

Ser Glu Asn Ala Thr Ala Lys Asp Ile Ala Pro Thr Leu Thr Leu Tyr
    210                 215                 220

Val Gly Lys Lys Gln Leu Val Glu Ile Glu Lys Val Val Leu His Pro
225                 230                 235                 240

Asn Tyr Ser Gln Val Asp Ile Gly Leu Ile Lys Leu Lys Gln Lys Val
                245                 250                 255

Ser Val Asn Glu Arg Val Met Pro Ile Cys Leu Pro Ser Lys Asp Tyr
            260                 265                 270

Ala Glu Val Gly Arg Val Gly Tyr Val Ser Gly Trp Gly Arg Asn Ala
        275                 280                 285

Asn Phe Lys Phe Thr Asp His Leu Lys Tyr Val Met Leu Pro Val Ala
    290                 295                 300
```

```
Asp Gln Asp Gln Cys Ile Arg His Tyr Glu Gly Ser Thr Val Pro Glu
305                 310                 315                 320

Lys Lys Thr Pro Lys Ser Pro Val Gly Val Gln Pro Ile Leu Asn Glu
                325                 330                 335

His Thr Phe Cys Ala Gly Met Ser Lys Tyr Gln Glu Asp Thr Cys Tyr
            340                 345                 350

Gly Asp Ala Gly Ser Ala Phe Ala Val His Asp Leu Glu Glu Asp Thr
        355                 360                 365

Trp Tyr Ala Thr Gly Ile Leu Ser Phe Asp Lys Ser Cys Ala Val Ala
        370             375             380

Glu Tyr Gly Val Tyr Val Lys Val Thr Ser Ile Gln Asp Trp Val Gln
385             390             395                 400

Lys Thr Ile Ala Glu Asn
                405
```

METHODS AND DEVICES FOR DIAGNOSIS OF APPENDICITIS

CROSS-REFERENCE TO RELATED APPLICATIONS

This application is a divisional application of U.S. application Ser. No. 11/189,120 filed Jul. 25, 2005, which claims priority to U.S. provisional application Ser. No. 60/590,631 filed Jul. 23, 2004, both of which prior applications are incorporated herein by reference to the extent not inconsistent herewith.

BACKGROUND OF THE INVENTION

Appendicitis is a common acute surgical problem affecting human beings of a wide age range. There are approximately 700,000 cases annually in the United States. A large proportion of cases occur in the 10 to 30 age group. An accurate diagnosis at a sufficiently early stage is a significant factor in achieving a successful outcome.

Many people present to their physician with symptoms suggestive of appendicitis but caused by other ailments such as viral infections. Differentiating the appendicitis patients from those affected with other ailments is a daunting clinical task that physicians face daily. While medical science has an excellent understanding of appendicitis and its treatment, it is very limited in its ability to accurately recognize or diagnose the disease.

Complicating the goal of an accurate and early diagnosis is the considerable overlap of genuine appendicitis with other clinical conditions. There appears to be no individual sign, symptom, test, or procedure capable of providing a reliable indication of appendicitis. Imaging technology is inadequate in identifying and characterizing the appendix, especially in the early stages of the disease when treatment is likely to be most effective. Imaging technology is further handicapped by its expense and its dependence upon the availability of highly trained and experienced people to interpret the studies. This limitation affects thousands of people every year by inaccurately diagnosing their problem or by delaying the accurate diagnosis. In cases of appendicitis, delays in diagnosis are the single most important factor leading to worsening of the condition and more complications related to the disease. The misdiagnosis of appendicitis can lead not only to unnecessary surgery but also to delay of proper therapy for the actual underlying condition.

A dilemma for surgeons is how to minimize the negative appendectomy rate without increasing the incidence of perforation among patients referred for suspected appendicitis. What is desperately needed to more effectively treat this very common ailment is a simple, reliable diagnostic test that is capable of recognizing the earliest stages of the disease process.

The typical pathogenesis in appendicitis begins with obstruction of the lumen, although an initial inflammation of the organ can precede and even contribute to the obstruction. The secreted mucus of the appendix fills the closed lumen, causing an increase in intralumenal pressure and distension. The increased intralumenal pressure can exceed the level of capillary perfusion pressure, resulting in perturbation of normal lymphatic and circulatory drainage. Ultimately the appendix can become ischemic. The appendix mucosa is compromised, which can allow invasion of intralumenal bacteria. In advanced cases, perforation of the appendix may also occur with spillage of pus into the peritoneal cavity.

Currently, the diagnosis of appendicitis is difficult, and the difficulty persists during various stages in the progression of the condition. The following represents a hypothetical portrayal of stages and associated clinical presentations. Artisans of ordinary skill will recognize that a considerable degree of variation will occur in a given patient population.

At the earliest stages of inflammation, a patient can present with a variety of non-specific signs and symptoms. Upon obstruction, presentation can involve periumbilical pain, mild cramping, and loss of appetite. The progress toward increased lumenal pressure and distension can be associated with presentation involving the localization of pain to the right lower quadrant of the abdomen, nausea, vomiting, diarrhea, and low grade fever. If perforation occurs, a patient can present with severe pain and high fever. At this very advanced stage, sepsis can be a serious risk with a potentially fatal outcome.

Practitioners currently use several tools to aid in appendicitis diagnosis. These tools include physical examination, laboratory tests, and other procedures. Routine laboratory tests include complete blood count (CBC) with or without differential and urinalysis (UA). Other tests include a computed tomography (CT) scan of the abdomen and abdominal ultrasonography. Procedures can include, for example, laparoscopic examination and exploratory surgery.

Flum et al. attempted to determine whether the frequency of misdiagnosis preceding appendectomy has decreased with increased availability of certain techniques (Flum D R et al., 2001). These techniques included computed tomography (CT), ultrasonography, and laparoscopy, which have been suggested for patients presenting with equivocal signs of appendicitis. Flum et al. concluded as follows: "Contrary to expectation, the frequency of misdiagnosis leading to unnecessary appendectomy has not changed with the introduction of computed tomography, ultrasonography, and laparoscopy, nor has the frequency of perforation decreased. These data suggest that on a population level, diagnosis of appendicitis has not improved with the availability of advanced diagnostic testing." The rate of misdiagnosis of appendicitis is about 9 percent in men and about 23.2 percent in women (Neary, W., 2001).

Myeloid-related Protein Complex 8/14 (MRP-8/14) is a heterodimeric complex associated with acute inflammatory conditions (for review see Striz and Trebichavsky, 2004). The complex belongs to the S100 superfamily of proteins and is also referred to S100A8/9, L1, macrophage inhibitory related protein and calprotectin. The heterodimer consists of an 8 kilodalton (MRP-8) and 14 kilodalton (MRP-14) subunit. MRP-8 and MRP-14 are alternatively named S100A8/calgranulin and S100A9/calgranulin b, respectively. MRP-8/14 is a calcium binding protein originally discovered in macrophages. Neutrophils expressing high concentrations of MRP-8/14 are found in a variety of inflammatory conditions, including rheumatoid arthritis, inflammatory bowel disease and allograft rejections (Frosch et al., 2000; Limburg et al., 2000; Burkhardt et al., 2001).

MRP-8/14 is not always diagnostic of inflammation. For example, it does not reliably indicate the presence of inflammatory diverticuli (Gasché, C. 2005). Lymphocytes do not generally contain MRP-8/14 (Hycult Biotechnology, Monoclonal Antibody to Human S100A8/A9), and therefore MRP-8/14 is not diagnostic of inflammation characterized by the presence of lymphocytes but not neutrophils. Also, this protein is not always associated with opportunistic infections (Froland, M. F., et al., 1994).

Haptoglobin is an acute phase protein that binds free hemoglobin following hemolysis. The haptoglobin-hemoglobin complex is removed by the liver. Haptoglobin is a heterotetramer composed of two alpha and two beta subunits. The alpha and beta units are derived from a single polypeptide chain precursor that is enzymatically cleaved to produce the subunits. The molecular weights of the subunits are approximately 9 kd-18 kd and 38 kd for alpha and beta, respectively.

In addition to being a hemoglobin scavenger, haptoglobin has a wide range of biological functions (Dobryszycka, 1997). Haptoglobin has been shown to be upregulated and modulate the immune response in certain infection and inflammatory conditions perhaps by regulating monocyte function (Arredouani et al., 2005). The alpha subunit has been demonstrated to be a potentially useful serum marker for ovarian cancer (Ye et al., 2003).

The ability to accurately diagnose appendicitis would be greatly augmented by the identification of molecules differentially associated with appendicitis.

SUMMARY OF THE INVENTION

This invention provides a method for diagnosing appendicitis in a patient comprising identifying at least one classical symptom of appendicitis in said patient and identifying the presence of at least one molecule differentially associated with appendicitis in a fluid or tissue sample of said patient. It is recognized in the art that the diagnosis of appendicitis is difficult, and that it is often misdiagnosed. Thus the term "diagnosing appendicitis" as used herein does not necessarily mean diagnosing appendicitis with more than usual accuracy. However, in fact, the methods of the present invention have been shown to provide improvements in correct diagnosis, with almost no false positives and few false negatives.

The term "differentially associated" with respect to a molecule "differentially associated with appendicitis" refers: (1) to a molecule present in a patient with appendicitis and not present in a patient not having appendicitis; (2) to a molecule whose relative level (amount) is distinguishing between appendicitis and non-appendicitis; (3) to a molecule present, or present at a level, in conjunction with the presence of other symptoms of appendicitis, that is diagnostic of appendicitis; and/or (4) to a molecule present, or present at a level, in conjunction with the lack of symptoms associated with conditions other than appendicitis in which the presence of the molecule occurs, that is diagnostic of appendicitis.

The diagnostic level of such a molecule is also referred to herein as the "threshold amount" or "threshold level." The molecules differentially associated with appendicitis are preferably protein antigens.

Classical symptoms of appendicitis include: pain in the abdomen; pain that starts near the navel, then moves to the lower right quadrant of the abdomen; anorexia (loss of appetite); trouble eating accompanied by sleepiness; nausea starting after onset of pain; vomiting starting after onset of pain; vomiting accompanied by fatigue; constipation; small stools with mucus; diarrhea; inability to pass gas; low-grade fever; abdominal swelling; pain in the abdomen worsening; tenesmus (feeling of needing to move the bowels); high fever; and leukocytosis. Increased plasma viscosity is also associated with appendicitis. In one embodiment of the invention at least two or more symptoms of appendicitis are identified.

In one embodiment of this invention patients are screened to determine whether or not they have an "interfering condition," i.e., another condition in which the molecule is present in the type of sample being tested. Patients are tested for the presence of the molecule if they do not have such an interfering condition; or are tested for the presence of appendicitis-diagnostic levels of the molecule if they do have such an interfering condition. Appendix-diagnostic levels when the patient has an interfering condition are levels higher than those present in patients who have the interfering condition but do not have appendicitis. Interfering conditions include recent allograft; septicemia; meningitis; pneumonia; tuberculosis; rheumatoid arthritis; gastrointestinal cancer; inflammatory bowel disease; skin cancer, periodontitis, preeclampsia, and AIDS.

A sample can be a fluid or tissue, and can contain whole blood, plasma, serum, milk, urine, saliva and/or cells. Fecal samples may also be used. Preferably tissue and fecal samples are liquefied before testing.

In one embodiment of this invention two or more molecules differentially associated with appendicitis are tested for. Identification of additional molecules provides greater accuracy to the method.

One molecule differentially associated with appendicitis is MRP-8/14. Another is haptoglobin. Both these molecules can be tested for in diagnosing appendicitis. MRP-8/14 levels in the range of about 1 to about 11 µg/ml are present in patients without appendicitis. Levels higher than this provide increased accuracy in diagnosing appendicitis. Levels higher than about 10, 11, 13, 15 or 20 µg/ml of MRP-8/14 can be used to diagnose appendicitis. Haptoglobin levels in the range of about 27-139 mg/dL are found in patients without appendicitis. Levels higher than this, e.g., higher than 125, 130, 135, 139 and 150 provide increased accuracy in diagnosing appendicitis.

Other molecules that can be tested for in the methods of this invention, or that can be tested for in addition to the foregoing molecules, include unique structural proteins of the gastrointestinal tract, stress-related inflammatory mediators, immunologic factors, indicators of intestinal bacterial flora, Plasminogen Activator Inhibitor-1, fatty acid binding proteins, nuclear factor kappa beta (NFKB), specific appendix antigens (HLA-DR), inflammation associated antigens; and nucleic acids coding for any of the foregoing, including nucleic acids coding for MRP-8/14 and haptoglobin. Methods for testing for the presence of nucleic acids are known to the art.

The methods of this invention involving obtaining a first sample from a patient suspected of having appendicitis can also comprise identifying at least one molecule differentially associated with appendicitis by a process including obtaining a second fluid or tissue sample from a second patient, wherein the second patient has appendicitis; obtaining a third fluid or tissue sample from a third patient wherein the third patient has a non-appendicitis condition characterized by at least one symptom of appendicitis; and analyzing the second and third samples so as to detect a molecule differentially associated with the appendicitis in the second patient, and then identifying the presence of that molecule, or presence of an increased level of that molecule, in the first sample, thereby diagnosing appendicitis. Candidate molecules for this process of identifying molecules differentially associated with appendicitis include unique structural proteins of the gastrointestinal tract, stress-related inflammatory mediators, immunologic factors, indicators of intestinal bacterial flora, Plasminogen Activator Inhibitor-1, fatty acid binding proteins, nuclear factor kappa beta (NFκB), specific appendix antigens (HLA-DR), inflammation associated antigens, and nucleic acids coding for any of the foregoing.

This invention also provides a method for identifying a molecule differentially associated with appendicitis, the method comprising obtaining a sample from each of a plurality of patients who are undergoing surgery for suspected appendicitis; determining during surgery whether each said patient has appendicitis or not; and analyzing said samples for the presence of a molecule differentially associated with appendicitis. The samples can be blood samples or samples of appendix tissue. This method can also include determining the amount of each molecule found to be differentially associated with appendicitis in the sample. In one embodiment of the invention, following identification of the molecule in tissue, it is also identified in plasma. This requires that samples of blood be taken from patients suspected of having appendicitis. The amount of the molecule differentially associated with appendicitis in patients who have appendicitis compared with those who do not is also determined.

The methods for diagnosing appendicitis of this invention can include using test devices, e.g., cartridge test devices and dipstick test devices, and/or other means for determining the presence or absence of a molecule differentially associated with appendicitis, e.g., performing western blots, northern blots, ELISA tests, protein function tests, PCR and other assays known to the art. In testing molecules differentially associated with appendicitis that are present in patients without appendicitis, but upregulated in patients with appendicitis, assays that test for the relative amount of the molecule present in patient fluids or tissues as well as the mere presence of the molecule are required. Cartridge immunoassays can be designed to provide information on relative amounts of such molecules as described herein. Other assays known to the art including ELISAs and hospital assay devices such as the Synchron LX system of Beckman Coulter can be used to provide the amount of such molecules present in the patient, which can then be compared with amounts present in patients without appendicitis to determine whether or not the patient has appendicitis.

The methods for diagnosing appendicitis can include performing an immunological assay using a monoclonal or polyclonal antibody to the molecule differentially associated with appendicitis. Such antibodies are known to the art or can be generated by means known to the art without undue experimentation.

This invention also provides an immunoassay test device for detecting the presence of a molecule differentially associated with appendicitis in a sample. The device comprises a first monoclonal or polyclonal antibody specific to the molecule, a support for the first monoclonal or polyclonal antibody, means for contacting the first monoclonal or polyclonal antibody with the sample, and an indicator capable of detecting binding of the first monoclonal or polyclonal antibody with the molecule.

Detecting binding of the antibody with the molecule can include binding the antibody/molecule complex to a second, labeled antibody which binds to the molecule or to the antibody of the complex.

Test devices can be in the form of cartridges, dipsticks, or other conformations known to the art. The test device can also be part of a kit which can contain instructions for use, instructions for comparison of test results with results of the same test done on non-appendicitis patient, additional reagents, such as cells or fluids from non-appendicitis patients, and other reagents known to the art. These types of assay devices are known to the art and described, e.g., in U.S. Patent Publication No. 2003/0224452.

The methods for diagnosing appendicitis can include comparing the level of the molecule in the sample with a background level of the same molecule in persons not having appendicitis. This comparison can be made by any means known to the art. It can include comparing sample results with results from a second sample taken from a person known not to have appendicitis, or comparing sample results with a photograph or other representation of results from a person not having appendicitis. Test devices having means for masking non-appendicitis levels, e.g. a support having the same color or tone as indicators showing non-appendicitis levels, or a filter having the same color or tone as a non-appendicitis level, so that only higher, appendicitis-indicating levels of the molecule are detectable, e.g., by eye, can also be used. The methods of this invention can include use of control fluids having background levels of the molecule typical of non-appendicitis samples, as well as colored supports and/or light filters as discussed above.

When the sample is blood, the method can also include processing the blood by a means known to the art, such as filtration or centrifugation, for separating plasma or serum which is to be assayed.

Antibody supports are known to the art. In an embodiment of this invention, antibody supports are absorbent pads to which the antibodies are removably or fixedly attached. In the devices of this invention, any indicator means known to the art to detect antibody binding with the molecule can be used. The indicator means can include second, labeled, monoclonal or polyclonal antibodies which bind to the selected protein, which preferably bind to a substantially different epitope on the selected protein from that to which the first monoclonal or polyclonal antibodies bind, such that binding of the first monoclonal or polyclonal antibody will not block binding of the second antibody, or vice versa. The indicator means can also include a test window through which labeled antibodies can be viewed. Any label known to the art can be used for labeling the second antibody. In an embodiment of this invention, the label is colloidal gold. The second antibody can be monoclonal or polyclonal. In an embodiment of this invention, the first antibody is a polyclonal or a monoclonal antibody made using a specific polypeptide sequence of the molecule differentially associated with appendicitis, and the second antibody is a different monoclonal or polyclonal antibody which binds to a different site of the molecule or binds to the first antibody. Antibodies for MRP-8 and MRP-14 are commercially available through Cell Sciences, Canton, Mass. Monoclonal antibodies to haptoglobin useful in the methods of this invention are also known to the art, e.g., as described in U.S. Pat. No. 5,552,295.

In one embodiment of this invention, the sample to be assayed is a liquid, and the immunoassay test device is a lateral flow device comprising inlet means for flowing a liquid sample into contact with the antibodies. The test device can also include a flow control means for assuring that the test is properly operating. Such flow control means can include control antigens bound to a support that capture detection antibodies as a means of confirming proper flow of sample fluid through the test device. Alternatively, the flow control means can include capture antibodies in the control region which capture the detection antibodies, again indicating that proper flow is taking place within the device.

Methods for detecting the presence of a molecule differentially associated with appendicitis using the foregoing devices are also provided, the methods comprising: providing an immunoassay test device of this invention; contacting a first antibody with a sample; and reading an indicator which is capable of detecting binding of the first antibody. Preferably, binding indicates appendicitis in the patient being tested. Methods of using these devices can be performed in the doctor's office, emergency room, or surgery, rather than requiring sending the patient or the sample to a separate laboratory.

The devices of this invention are useful for testing the above-mentioned samples. When cells are tested, e.g., when the molecule differentially associated with appendicitis is suspected to be in blood or tissue cells rather than serum, the method and/or device can include a cell-lysing step or means using detergent, puncture or other physical or chemical process known to the art.

DETAILED DESCRIPTION

Figure 1A:
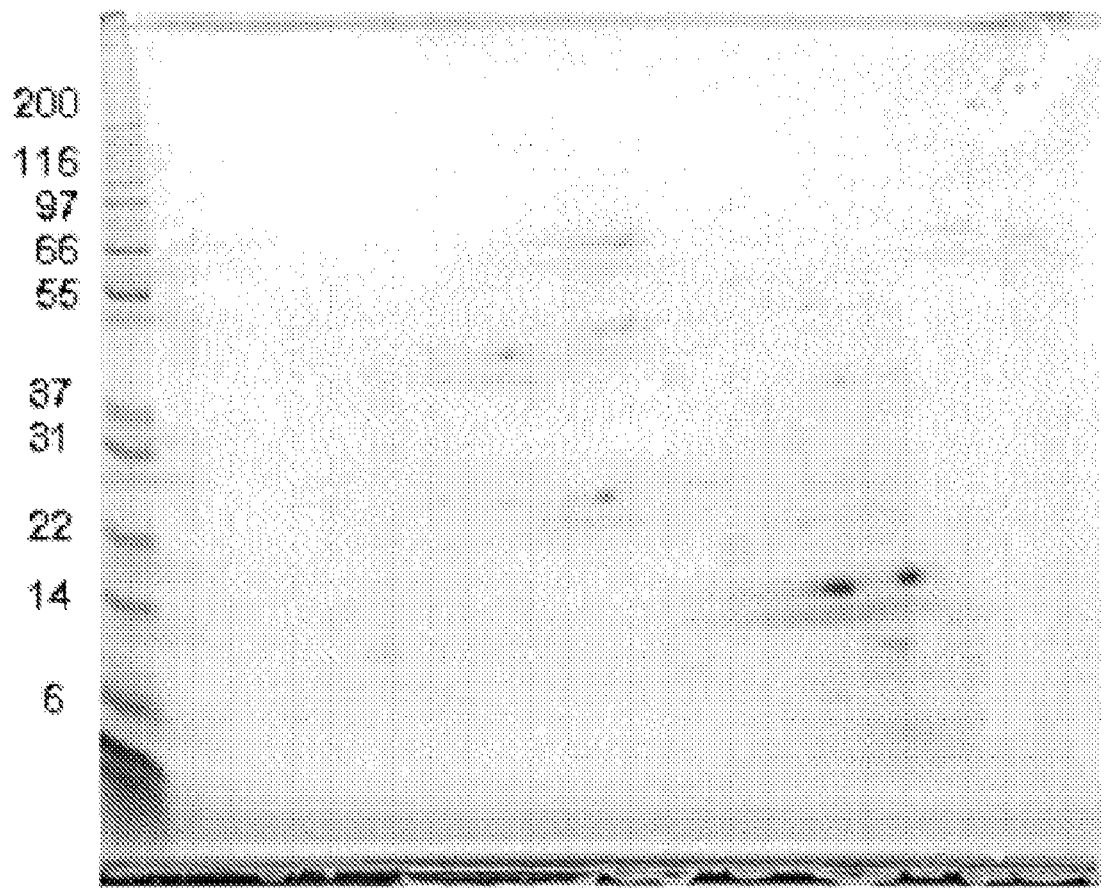
FIG. 1: Two-dimensional electrophoresis image of proteins from (A) normal and (B) diseased appendix tissue. Proteins were separated by isoelectric focusing on the x axis and by molecular weight on the y axis. The molecular weight in kilodaltons is shown on the left. The arrow indicates the upregulated protein, AP-93.

The vermiform appendix is recognized as a separate organ from the large and small intestines. It extends as a finger-like pouch from the base of the ascending colon, which is also called the cecum. The appendix, like the large intestine, is hollow and composed of the same three tissue layers. These three layers are a mucosa, muscularis and a serosa. The appendiceal lumen communicates with the lumen of the cecum via a round opening (os) through which the appendix adds its secretions to the fecal stream. These secretions are excess mucus produced from the appendiceal mucosa. In addition to containing mucus, the appendix also contains numerous bacteria common to the right colon. Obstruction of the appendiceal lumen is the dominant factor causing acute appendicitis. While fecaliths are the usual cause of appendiceal obstruction, hypertrophied lymphoid tissue, inspissated barium from previous x-ray studies, vegetable and fruit seeds, and intestinal worms like ascarids can also block the appendiceal lumen.

Following luminal obstruction an escalating cycle of events ensues. The proximal obstruction of the appendix produces a closed-loop obstruction that blocks the normal flow of appendiceal mucus into the cecum. The continuing normal secretion of the appendiceal mucus very rapidly fills the luminal capacity of the appendix (approximately 0.1 cc). Once the luminal capacity of the appendix is reached additional mucus production from the obstructed appendix rapidly elevates the intraluminal pressure within the organ. This elevated intraluminal pressure is exerted outward against the appendiceal wall and causes the appendix to distend. Distention stimulates nerve endings of the visceral afferent pain fibers, producing vague, dull, diffuse pain in the midabdomen or lower epigastrium. Peristalsis is also stimulated by the rather sudden distention, so that some cramping may be superimposed on the visceral pain early in the course of appendicitis.

Distention of the appendix continues, not only from continued mucosal secretion, but also from rapid multiplication of the resident bacteria of the appendix. As pressure in the organ increases, venous pressure within the appendiceal wall is exceeded. This rising intraluminal pressure then occludes capillaries and venules, but arteriolar inflow continues, resulting in engorgement and vascular congestion. Distention of this magnitude usually causes reflex nausea and vomiting, and the diffuse visceral pain becomes more severe. The inflammatory process soon involves the serosa of the appendix and in turn parietal peritoneum in the region, producing the characteristic shift in pain to the right lower quadrant (RLQ). The disease process is fairly advanced when pain is localized to the RLQ.

The mucosa of the gastrointestinal tract, including the appendix, is very susceptible to impaired blood supply. Thus mucosal integrity is compromised early in the process, allowing bacterial invasion of the deeper tissue layers. This bacterial invasion leads to appendiceal destruction and systemic liberation of various bacterial toxins. Fever, tachycardia, and leukocytosis develop as a consequence of this systemic release of dead tissue products and bacterial toxins. As progressive appendiceal distention rises, encroaching on the arteriolar pressure, ellipsoidal infarcts develop in the antimesenteric border of the appendiceal serosa. As distention, bacterial invasion, compromise of vascular supply and infarction progress, perforation occurs through one of the infarcted areas on the antimesenteric border. This perforation then releases the bacteria and its toxins into the abdominal cavity.

Appendicitis has been called the "great imitator," as its symptoms are frequently confused with those of other conditions. This confusion stems from the nonspecific nature of the pain early in its course and the variability in how appendicitis progresses. Pain in the right lower quadrant of the abdomen is the hallmark of appendicitis but this is not typically what the patient first perceives. When the appendiceal lumen first obstructs, the patient will have few if any symptoms because the appendiceal lumen has not yet had the chance to fill with mucus. The time required to fill the appendiceal lumen is proportional to the lumen volume available behind the obstruction. This is variable and unpredictable, as that volume is dependent upon the individual's appendix size and precisely where the fecalith or other obstruction is located along that length. Should the fecalith or other obstruction be close to the tip of the appendix the available volume is relatively small and the time to symptoms or perforation short. In contrast, the opposite will be true should the fecalith or other obstruction be near the base of the appendix and provide for the largest possible appendiceal volume.

Once the appendix begins to distend, the appendicitis patient will begin to experience a nonspecific discomfort usually in the mid portion of the abdomen. This discomfort can be easily confused with common ailments such as indigestion, constipation or a viral illness. Continued appendiceal distention is also accompanied by some nausea and frequently vomiting. Rarely is the vomiting severe or unrelenting, which reinforces the confusion with common ailments.

Later in the progression of appendicitis, inflammation will have progressed to the outermost layer of the appendix. This outmost layer is called the serosa and it touches the inner lining of the abdominal cavity called the peritoneum. This contact irritates the peritoneum, producing peritonitis that is perceived by the appendicitis patient as focal pain wherever the appendix is touching the peritoneum. This too can vary between different individuals. The appendix is most usually located in the right lower quadrant under an area known as McBurney's point. McBurney's point is a position on the abdomen that is approximately two-thirds of the distance from the anterior superior iliac spine in a straight line toward the umbilicus. The appendix can, however, reside in other locations in which case the peritonitis produced by the appendix will be in an atypical location. This again is a common factor producing an erroneous diagnosis and delays surgical treatment in cases of appendicitis.

Regardless of its location, if appendicitis is allowed to progress the organ will eventually perforate. This contaminates the abdominal cavity around the perforated appendix with bacteria producing a severe infection. This infection will usually lead to a localized intra-abdominal abscess or phlegmon and can produce generalized sepsis.

To identify molecules differentially associated with appendicitis, a proteomic approach was used. A protein complex, MRP-8/14, that is present in appendix tissue in patients with acute appendicitis was identified. The highly correlative nature of this complex with appendicitis led us to examine MRP-8/14 serum levels in patients with apparent appendicitis. MRP-8/14 is significantly elevated ($p<0.02$) in patients with appendicitis as compared to levels in patients with apparent appendicitis yet having no appendiceal inflammation. The source of MRP-8/14 in the serum is the inflamed appendix tissue. This is consistent with the known functions of MRP-8/14.

The role of MRP-8/14 in inflammation is not fully understood but it does seem to play a vital role in retaining leukocytes in microcapillaries. Extracellular MRP-8/14 interacts with endothelial cells by binding to heparin sulfate and specifically carboxylated glycans (Robinson et al., 2002). The intracellular signal pathways and effector mechanisms induced by binding of MRP-8/14 to endothelial cells are not well defined. However, interaction of MRP-8/14 with phagocytes increases binding activity of the integrin receptor CD11b-CD18. This is one of the major adhesion pathways of leukocytes to vascular endothelium (Ryckman et al., 2003). It is believed that the MRP-8/14 utilizes the receptor for advanced glycation end products (RAGE). A relative of MRP-8/14, S100A12, is a specific ligand of RAGE expressed by endothelial cells and their interaction activates NF-kappa B binding in these cells (Hsieh et al., 2004). The NF-kappa B binding subsequently induces expression of many proinflammatory molecules, such as various cytokines or adhesion molecules. Thus, release and extracellular functions of S100 proteins represent a positive feedback mechanism by which phagocytes promote further recruitment of leukocytes to sites of inflammation. Taken together, these proteins appear to play a role in a fundamental inflammatory response in certain inflammatory conditions, and are excellent markers of appendix tissue inflammation.

Neutrophils are white blood cells that are the first to migrate from the circulation into sites of inflammation. Within neutrophils, constituting approximately 40% of total cytosolic proteins is the MRP-8/14 complex. This protein is specifically expressed only in cells of macrophage lineage, making blood monocytes and acutely activated macrophages other potential white blood cell sources of these proteins. MRP-8/14 is not usually expressed in lymphocytes nor resident macrophages or those macrophages involved in chronic inflammation. These two proteins are also known to be independently expressed by mucosal epithelium in specific states of acute inflammation.

In the case of appendicitis, the luminal obstruction and the resultant distention of the appendiceal wall triggers an inflammatory response. The circulating neutrophils are then recruited into the area, as are activated macrophages. While the expression of this protein complex is related to the activity of the macrophages in inflammation, the exact relationship between MRP-8/14 and cellular activity is not fully known. What is known is that the intracellular distribution of MRP-8/14 varies with the activation state of macrophages. Normal macrophages contain the complexes in the cytosol, but once stimulated, MRP-8/14 translocates from the cytosol to the cell membrane (specifically with the proteins of the cytoskeleton). This would imply that MRP-8/14 may be related to cell movement, phagocytosis or inflammatory signal transduction. The roles of cellular movement and signal transduction may also explain why MRP-8/14 is produced directly from vascular epithelium such as that lining the blood vessels within the appendix.

Regardless of its role in certain inflammatory conditions, MRP-8/14's abundance within cells of acute inflammation makes it an excellent detector and monitor of acute appendicitis. The first step in the inflammatory process is the recruitment of neutrophils and macrophages to a specific site. In our study, the specific site is the appendix, where those MRP-8/14-containing cells will engage the offending stimulus. This engagement will usually result in MRP-8/14 cell death and the liberation of MRP-8/14 from either the cytosol or cell membrane into the patient's circulation. At the same time, the mucosal linings of the appendix will start to produce and release MRP-8/14 to facilitate macrophage migration or inflammatory amplification. This process will then escalate as increasing amounts of MRP-8/14 cells are recruited by the appendicitis to ultimately release more MRP-8/14 into the circulation. Other examples of inflammatory states causing increases of extracellular MRP-8/14 and the tendency of these increases of MRP-8/14 to correlate with extent of inflammation are known. Specifically, chronic bronchitis, cystic fibrosis and rheumatoid arthritis are all associated with elevated serum levels of MRP-8/14 and the severity of these diseases is generally proportional to the serum levels of MRP-8/14 detected.

The physiological role of MRP-8/14 makes it an ideal clinical marker for acute appendicitis. As patients with appendicitis are generally young and healthy, they generally produce a vigorous inflammatory response. This vigorous response is believed to liberate MRP-8/14 in the earliest stages of the disease, which then escalates as appendicitis progresses. Additionally, the diseases known to be associated with elevated levels of MRP-8/14 are not common in this younger age group and usually do not produce symptomology similar to appendicitis. Finally, as MRP-8/14 is not located in nor associated with lymphocyte proliferation, this marker is not believed to be elevated in viral infections. This is an especially powerful advantage for diagnosing appendicitis, as viral infections are one of the most common imitators of appendicitis.

Haptoglobin was also identified in this invention as a useful marker for appendicitis. A differential proteomic screen of depleted serum identified haptoglobin as a marker for appendicitis. A second differential screen of appendix tissue confirmed that haptoglobin is upregulated in the appendix tissue of patients with appendicitis. This finding was confirmed by western blotting of tissue protein. In particular the alpha subunit isoforms were present only in diseased tissue. Since haptoglobin is a plasma protein, it is highly valuable as a biomarker for appendicitis.

EXAMPLES

Example 1

MRP-8/14

The objective of this study was to identify a tissue-specific marker that could contribute to the decision matrix for diagnosing early acute appendicitis. A proteomic screen was used to identify a protein in the appendix specifically upregulated in acute appendicitis. MRP-8/14 was identified as present both in the diseased appendix and in serum of acute appendicitis patients.

Materials and Methods

Specimen and Serum Collection. All patients enrolled in this study were treated according to accepted standards of care as defined by their treating physicians. Prior to being approached for inclusion in our study, all patients were evaluated by a surgeon and diagnosed by that surgeon as having appendicitis. The treating surgeon's plans for these appendicitis patients included an immediate appendectomy. The specifics of all treatments such as use of antibiotics, operative technique (either open or laparoscopic) were determined by the individual surgeon.

Exclusion Criteria Any patients with pre-existing chronic inflammatory diseases such as asthma, rheumatoid arthritis, inflammatory bowel disease, psoriasis, or neutropenia. Pregnancy was also considered an exclusion criterion.

An investigator counseled all patients about the study and informed consent was obtained. At the time of informed consent, the subject was assigned an identification number and non-personal demographic and clinical information was obtained (age, sex, race, duration of symptoms, white blood count (WBC), results of imaging studies, etc). At the time of surgery, following induction of general anesthesia, a whole blood sample (5-10 cc volume) was obtained via peripheral venopuncture. This blood specimen was then placed on ice. As soon as possible, a small sample (approximately 1 gram) of inflamed appendix was taken from the pathologic specimen and also placed on ice. The iced blood specimens were then centrifuged for 20 minutes at 3000 rpm and the separated serum isolated. This isolated serum and the piece of appendix tissue were then stored separately, frozen at −80° C.

Appendicitis Tissue Processing. Appendix tissue from appendectomy patients was harvested and stored at −80° C. until processed. Individual tissue samples were ground into powder using a sterile mortar and pestle under liquid nitrogen. Protein was extracted from tissue powder by incubating at 37° C. in Extraction Buffer (0.025M Tris-base, 200 mM Sodium Chloride, 5 mM EDTA, 0.1% Sodium Azide, pH 7.5). Samples were centrifuged for 10 minutes at 14K rpm. Supernatants were stored at −80° C. until analysis.

2D Gel Analysis of Extracted Tissue Samples. 2D gel analysis was performed on depleted serum samples and extracted tissue samples. Isoelectric focusing (IEF) and SDS-PAGE were performed according to the Zoom (Invitrogen) protocol for 2D Gel analysis. Equal quantities of protein were analyzed on each gel.

Comparisons between negative serum gel and positive serum gel were made to determine which proteins were present in positive samples and absent in negative samples. Candidate gel spots were identified and submitted to MALDI-TOF protein identification analysis (Linden Biosciences).

Western Blot Analysis of Extracted Appendix Tissue Samples. Samples (10 μg) were subjected to standard Laemmli SDS-PAGE and proteins were transferred to nitrocellulose membrane for western blot analysis using standard techniques with chemiluminescent detection. Magic Mark Western Standard (Invitrogen) was used to determine molecular weight. MRP-8 (Calgranulin A C-19, Santa Cruz, S.C.-8112) was used in a 1:100 dilution in 0.5× Uniblock (AspenBio, Inc) for primary antibody. The secondary antibody was Peroxidase anti-goat IgG (H+L), affinity purified (Vector, PI-9500) in a 1:2000 dilution in Uniblock. MR-14 (Calgranulin B C-19, Santa Cruz, S.C.-8114) was used in a 1:100 dilution in 0.5× Uniblock for primary antibody. The secondary antibody was Peroxidase anti-goat IgG (H+L), affinity purified (Vector, PI-9500) in a 1:2000 dilution in Uniblock.

Serum MRP-8/14 Determinations. Serum levels of MRP-8/14 were determined by ELISA using a commercially available ELISA (Buhlmann S100-Cellion S100 A8/A9) according to the manufacturer's protocol.

Results

Identification of Proteins Present in Appendix Tissue from Appendicitis Patients. A differential proteomic analysis was performed on depleted serum samples with the goal of identifying proteins elevated in patients with acute appendicitis. The analysis involved comparing samples from normal patients versus patients with perforated appendices. Blood samples were obtained immediately prior to surgery. A normal patient in this study is one that presented with abdominal pain, underwent surgery, and was found to have a normal appendix. Normal and diseased appendix tissue was collected during surgery.

Figure 1B:
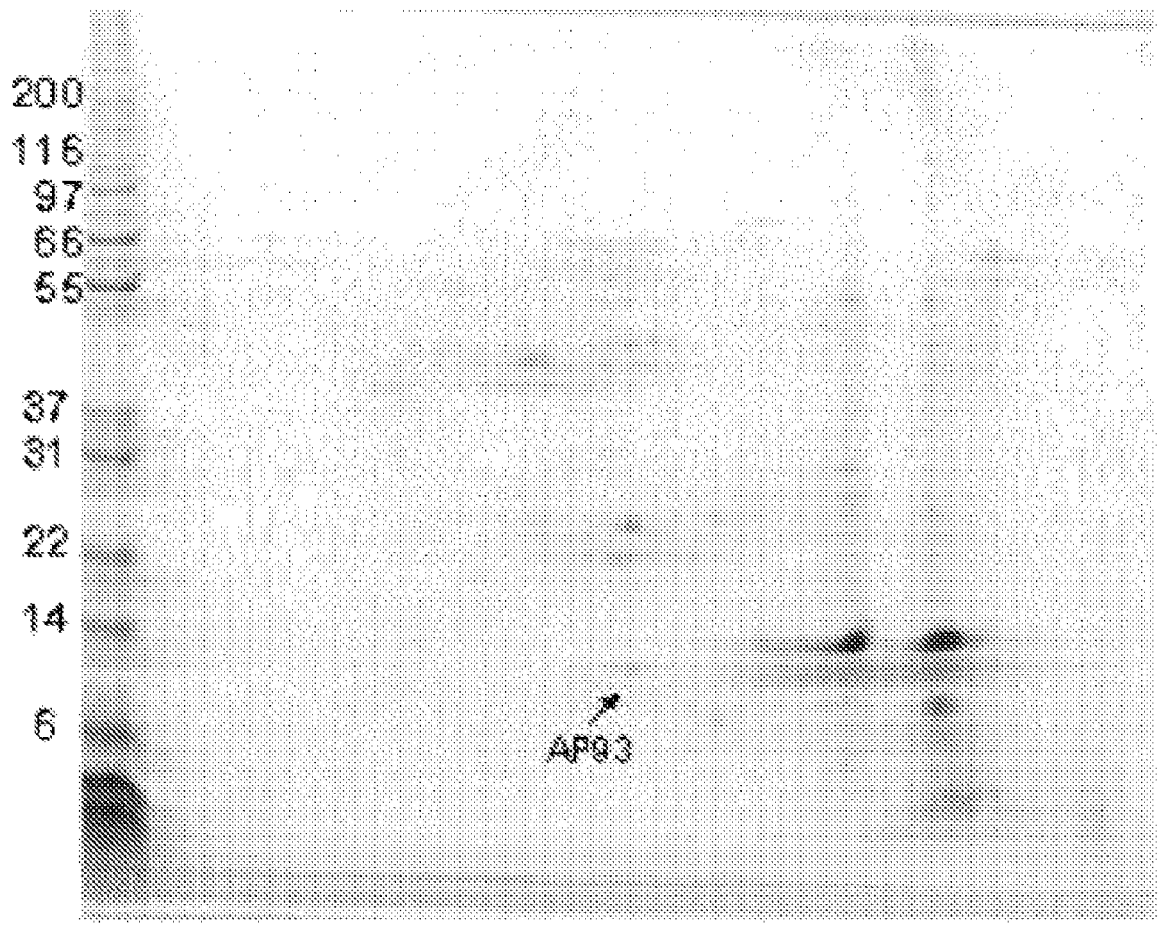

The proteomic approach was to compare a pool of 4 normal samples with a pool of 4 appendicitis samples using two-dimensional electrophoresis. FIG. 1 shows the 2D profile of proteins analyzed. Comparison between the gels was performed and the most obvious difference is indicated in FIG. 1B as AP-93. Based on the gel in FIG. 1, the molecular weight of AP-93 is approximately 14 kilodaltons. The corresponding gel slice was analyzed by MALDI-TOF and a positive identification was made. The identification was based upon spectra of two tryptic peptides, NIETIINTFHQYSVK [SEQ ID NO:1] and LGHPDTLNQGEFKELVR [SEQ ID NO:2]. The peptides correspond to the underlined residues in the following amino acid sequence of MRP-14 (GenBank Accession Number P06702):

[SEQ ID NO:3]
MTCKMSQLERNIETIINTFHQYSVKLGHPDTLNQGEFKELVRKDLQNFLK

KENKNEKVIEHIMEDLDTNADKQLSFEEFIMLMARLTWASHEKMHEGDEG

PGHHHKPGLGEGTP.

The MALDI-TOF identification of AP-93 as MRP-14 was confirmed by the matching molecular weights. Based on this data, MRP-14 protein was more highly abundant in the diseased sample pool than in the normal sample pool.

Figure 2:
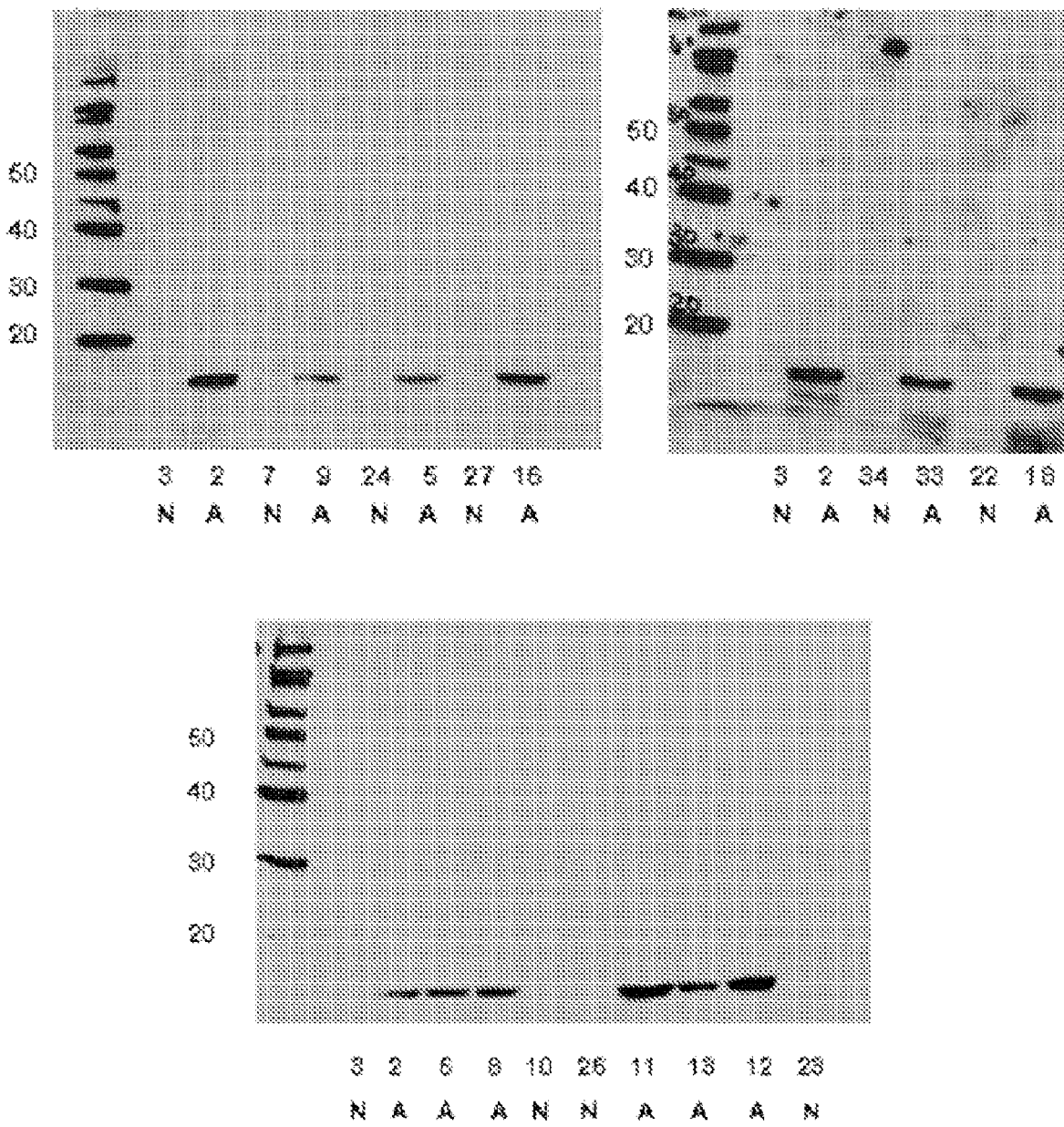
FIG. 2: MRP-14 western blot analysis of normal (N) and diseased (A) tissue. The numbers are sample ID numbers. Molecular weights are shown in kilodaltons.

Presence of MRP-14 and MRP-8 in Diseased Appendix Tissue. In order to confirm the presence of MRP-14 in diseased tissue, an anti-MRP-14 antibody was used in western blotting of tissue extracts from individual normal and diseased appendices. FIG. 2 shows the western blot data from 9 normal and 11 appendicitis samples. A 14 kilodalton band is present in every appendicitis sample. There is no detectable signal in the normal samples. This data confirms the proteomic screen data and shows that the protein is an indicator of diseased appendix tissue.

Figure 3:
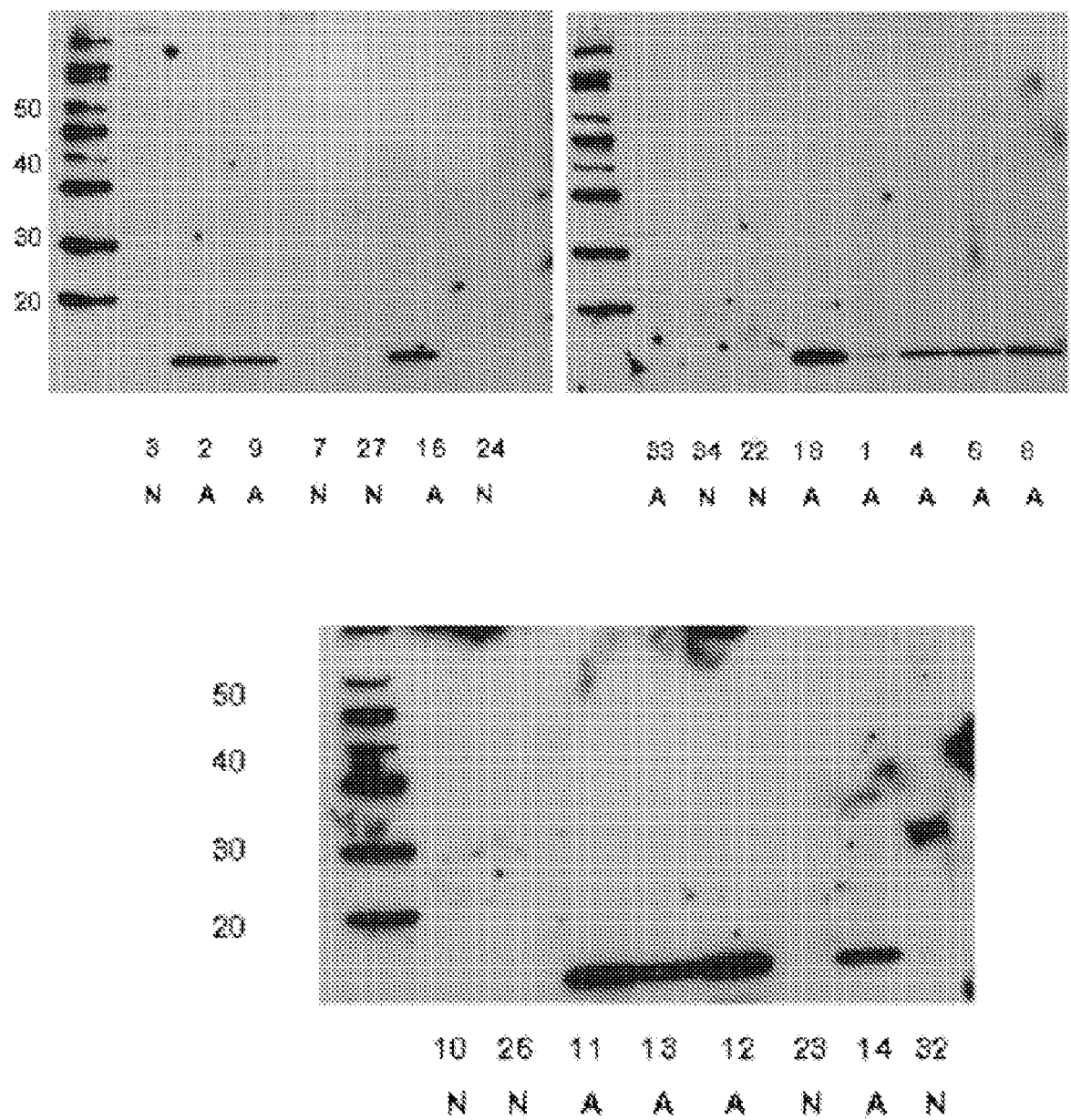
FIG. 3: MRP-8 western blot analysis of normal (N) and diseased (A) tissue. The numbers are sample ID numbers. Molecular weights are shown in kilodaltons.
Figure 4:
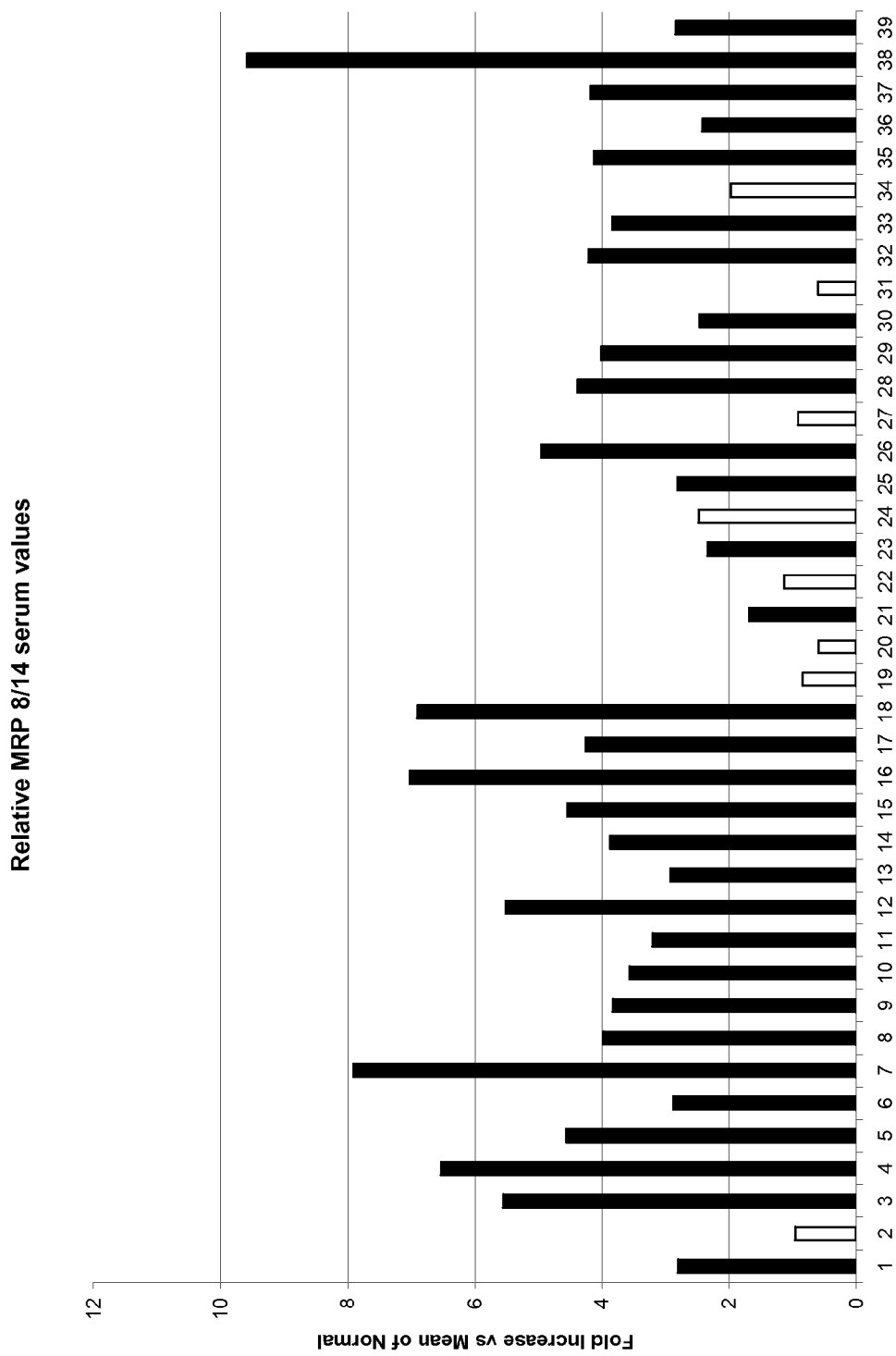
FIG. 4: Relative levels of MRP-8/14 in normal and appendicitis serum as determined by ELISA. The levels are given as a fraction of the mean for the patients not having appendicitis, said fraction also being referred to herein as a "fold increase." Dark bars represent samples from patients having appendicitis. White bars represent samples from patients not having appendicitis.

Since it is known that MRP-8 exists as a dimer with MRP-14, tissue specimens were also examined for the presence of MRP-8. FIG. 3 shows the western blot data using an anti-MRP-8 antibody on the normal and diseased tissue samples. As expected, MRP-8 is present in all of the diseased appendix samples and not detectible in the normal appendix tissue. These western blot data show that the MRP-8 and MRP-14 proteins are markedly more abundant in appendicitis than in normal appendix tissue.

Elevated Serum Levels of MRP-8/14 Patients with Acute Appendicitis. The high correlation between appendicitis and the presence of MRP-8/14 in the appendix led us to examine the MRP-8/14 levels in serum of those patients and other patients subsequently added to the study. The sera were collected before surgery, banked and analyzed after the disease status was known. MRP-8/14 levels were measured using a sandwich ELISA specific for the complex.

Table 1 lists serum MRP-8/14 levels for 39 patients as determined by an ELISA manufactured by Hycult (Netherlands) and available commercially through Cell Sciences, Canton, Mass. The amounts are given as fractions compared to an average level for patients in the study without appendicitis. Note that all patients with appendicitis show a fold-increase of MRP-8/14 over average normal levels. The procedure was conducted according to instructions accompanying the ELISA product. The sample numbers do not correspond to the sample numbers shown in FIGS. 2 and 3 as the samples were renumbered.

TABLE 1

| Sample Number | Clinical Diagnosis | Pathology | Grading | Fraction of Normal |
|---|---|---|---|---|
| 1 | Advanced Appendicitis | Mild Acute Appendicitis | 2 | 2.80428 |
| 2 | Normal Appy | Normal | 1 | 0.960805 |
| 3 | Advanced Appendicitis | Transmural Appendicitis | 3 | 5.554904 |
| 4 | Perforated Appy | Perforated Appy-Necrosis | 4 | 6.53913 |
| 5 | Early Appy | Mild Acute Appendicitis | 2 | 4.562059 |
| 6 | Early Appy | Mild-Acute Appendicitis | 1 | 2.881124 |
| 7 | Horrible perforated | Perforated Appy-Necrosis | 4 | 7.906886 |
| 8 | Normal Appy | Mild Acute Appendicitis | 2 | 3.971489 |
| 9 | Early Appy | Transmural Appendicitis | 3 | 3.83328 |
| 10 | Advanced Appendicitis | Transmural Appendicitis | 3 | 3.566665 |
| 11 | Appendicitis | Mild Acute Appendicitis | 2 | 3.205335 |
| 12 | Appendicitis | Transmural Appendicitis | 3 | 5.51224 |
| 13 | Advanced Appendicitis | Transmural Appendicitis | 3 | 2.92671 |
| 14 | Advanced Appendicitis | Transmural Appendicitis w Necrosis | 4 | 3.866306 |
| 15 | PERFORATED | Transmural Appendicitis | 3 | 4.54657 |
| 16 | Advanced Appendicitis | Perforated Appy | 4 | 7.01877 |
| 17 | Advanced Appendicitis | Transmural Appendicitis | 3 | 4.25998 |
| 18 | Appendicitis | Transmural Appendicitis | 3 | 6.90312 |
| 19 | Normal Appy | Normal | 1 | 0.838679 |
| 20 | Normal Appy | Normal | 1 | 0.590095 |
| 21 | Early Appy | Appendicitis with Peri appy changers | 3 | 1.682291 |
| 22 | Normal Appy | Normal | 1 | 1.128849 |
| 23 | Advanced appendicitis | Transmural Appendicitis | 4 | 2.338583 |
| 24 | Normal Appy | Normal | 1 | 2.478035 |
| 25 | Hot appy | | | 2.807046 |
| 26 | Perforated | Perforated | 4 | 4.954136 |
| 27 | Normal | Normal | 1 | 0.918438 |
| 28 | Hot | Hot | 2 | 4.387589 |
| 29 | Early | Transmural Appendicitis | 3 | 4.015013 |
| 30 | Hot | Transmural Appendicitis | 3 | 2.460902 |
| 31 | Normal | Normal | 1 | 0.594943 |
| 32 | Hot | Transmural Appendicitis | 3 | 4.211086 |
| 33 | Perforated | Transmural Appendicitis | 4 | 3.835219 |
| 34 | Normal | Normal | 1 | 1.968859 |
| 35 | Perforated | Transmural Appendicitis | 4 | 4.126198 |
| 36 | Advanced | Transmural Appendicitis | 3 | 2.423726 |
| 37 | Hot Appy | Transmural Appendicitis | 3 | 4.178647 |
| 38 | Early | Transmural Appendicitis | 3 | 9.584398 |
| 39 | Normal | Transmural Appendicitis | 2 | 2.835339 |

We have identified a protein complex that is present in the appendix and serum of appendicitis patients. Based on the western blot data, the presence of MRP-8/14 in appendix tissue is highly correlative with disease. Furthermore, levels of MRP-8/14 in serum are predictive of appendicitis. We presume that this increase is due to increased production of these proteins from systemic neutrophil infiltration of the appendix and possibly direct mucosal production of the proteins by the appendix itself. This study demonstrates that MRP-8/14 is a useful clinical marker for acute appendicitis. After our discovery that MRP-8/14 was a molecule differentially associated with appendicitis, our work was confirmed by the finding of Power, C. et al., 2004 and 2005, who reported detection of this molecule in feces of patients having acute appendicitis.

Example 2

Haptoglobin

Using a proteomic screen of serum and appendix tissue, we determined that haptoglobin is upregulated in patients with acute appendicitis. The alpha subunit of haptoglobin is an especially useful marker in screening for the disease.

Materials and Methods

Specimen and serum collection, appendicitis tissue processing, 2D gel analysis of extracted tissue samples, and western blot analysis of extracted appendix tissue samples were as described above in Example 1, except that for the western blot, affinity-purified anti-human haptoglobin (Rockland, 600-401-272) was used at a 1:5000 dilution in 0.5× uniblock for the primary antibody; and the secondary antibody was peroxidase anti-rabbit IgG (h+l), affinity purified (vector, pi-1000) in a 1:5000 dilution in uniblock.

Results

Identification of proteins present in appendix tissue from appendicitis patients. A differential proteomic analysis was performed on depleted serum samples with the goal of identifying proteins elevated in patients with acute appendicitis. The analysis involved comparing samples from normal patients versus patients with perforated appendices. Blood samples were obtained immediately prior to surgery. A normal patient in this study is one that presented with abdominal pain, underwent surgery, and was found to have a normal appendix. Normal and diseased appendix tissue was collected during surgery.

Figure 5A:
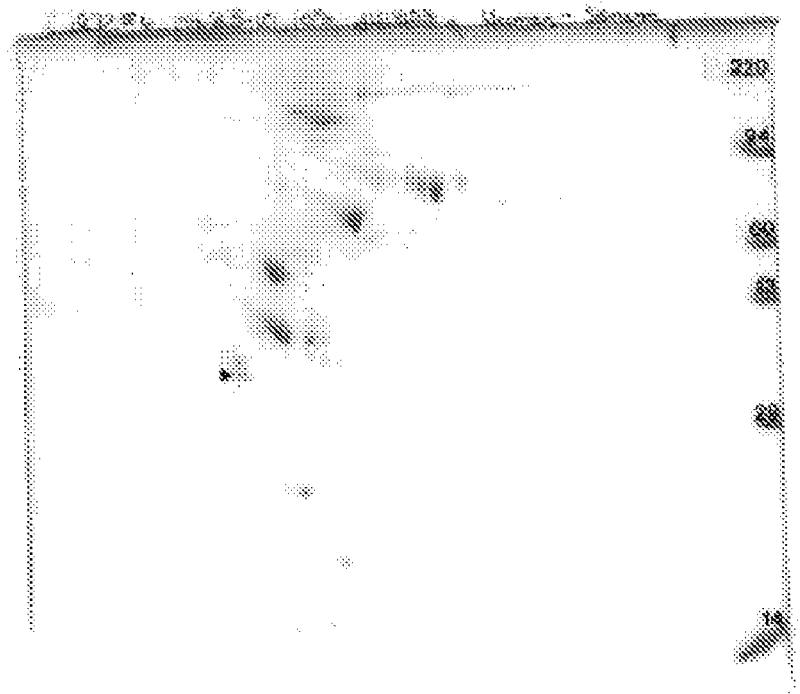
FIG. 5: Two-dimensional electrophoresis image of proteins in depleted serum samples from (A) normal and (B) appendicitis patients. Proteins were separated by isoelectric focusing on the x-axis and by molecular weight on the y-axis. The molecular weight in kilodaltons is shown in the right. The tailed arrow indicates the upregulated protein, AP-77 (haptoglobin alpha subunit). The untailed arrow indicates a control protein that is equally abundant in diseased vs. normal.
Figure 5B:
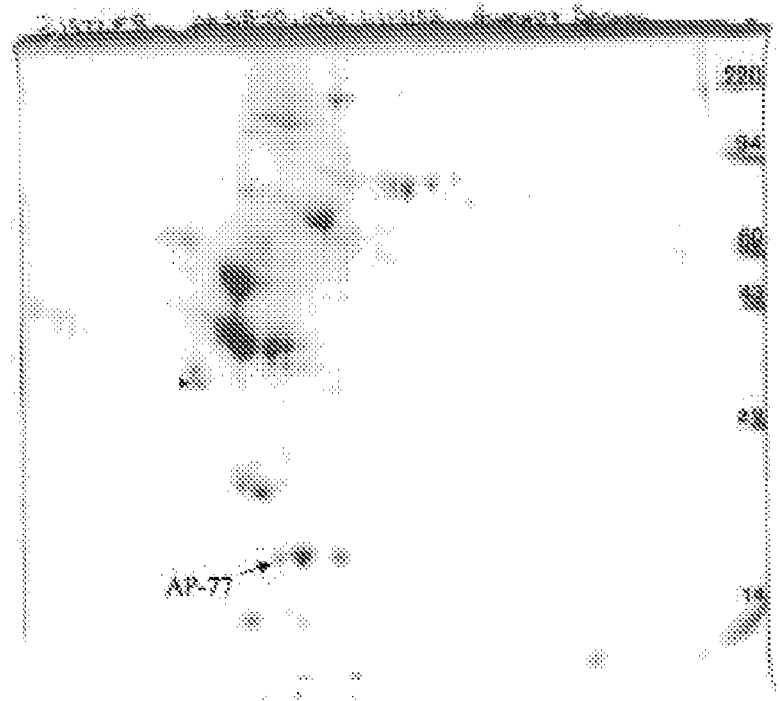

The proteomic approach was to compare a pool of 4 normal samples with a pool of 4 appendicitis samples using two-dimensional electrophoresis. FIG. 5 shows the 2D profile of proteins analyzed from serum depleted of IgG and albumin. Comparison between the gels was performed and the most obvious difference is indicated in FIG. 5B as AP-77. The protein in gel spot AP-77 was digested with trypsin and analyzed by MALDI-TOF. The resulting two peptides have the following sequences: TEGDGVYTLNNEKQWINK [SEQ ID NO:4] and AVGDKLPECEADDGCPKPPEIAHGYVE-HSVR [SEQ ID NO:5]. The sequences were aligned with the alpha subunit of haptoglobin. The sequence of haptoglobin precursor (GenBank Accession Number NP005134) is shown below with the tryptic fragments underlined.

[SEQ ID NO:6]
MSALGAVIALLLWGQLFAVDSGNDVTDIADDGCPKPPEIAHGYVEHSVRY

QCKNYYKLRTEGDGVYTLNDKKQWINKAVGDKLPECEADDGCPKPPEIAH

GYVEHSVRYQCKNYYKLRTEGDGVYTLNNEKQWINKAVGDKLPECEAVCG

KPKNPANPVQRILGGHLDAKGSFPWQAKMVSHHNLTTGATLINEQWLLTT

AKNLFLNHSENATAKDIAPTLTLYVGKKQLVEIEKVVLHPNYSQVDIGLI

KLKQKVSVNERVMPICLPSKDYAEVGRVGYVSGWGRNANFKFTDHLKYVM

LPVADQDQCIRHYEGSTVPEKKTPKSPVGVQPILNEHTFCAGMSKYQEDT

CYGDAGSAFAVHDLEEDTWYATGILSFDKSCAVAEYGVYVKVTSIQDWVQ

KTIAEN.

Figure 6A:
FIG. 6: Two-dimensional electrophoresis image of proteins from (A) normal and (B) diseased (perforated) appendix tissue. Proteins were separated by isoelectric focusing on the x axis and by molecular weight on the y axis. The molecular weight in kilodaltons is shown on the left. The arrow indicates the upregulated protein, AP-91 (haptoglobin alpha subunit).
Figure 6B:
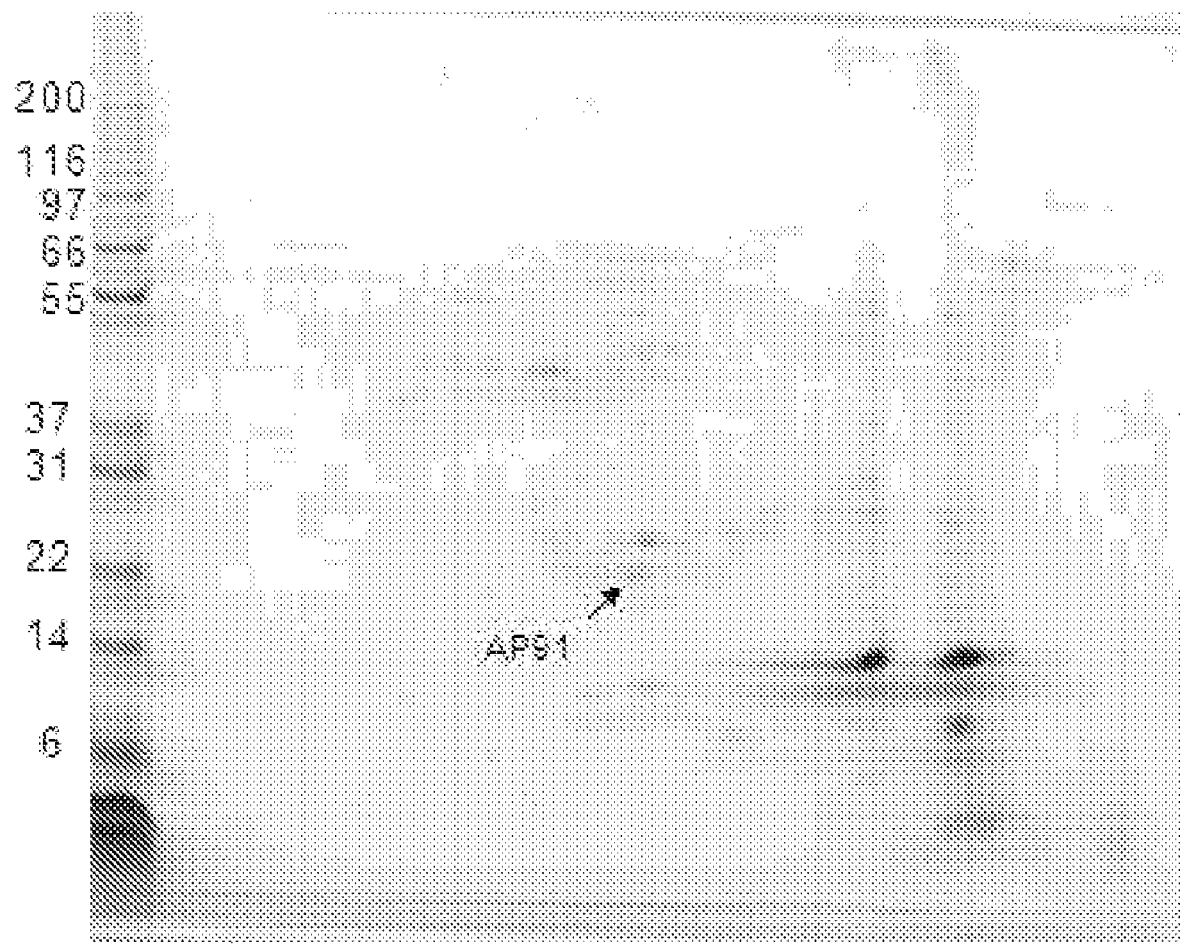

FIG. 6 shows the two-dimensional electrophoresis profile comparison between diseased and normal appendix tissue proteins. Two spots, AP-91 and AP-93, were analyzed by MALDI-TOF and positive identifications were determined. AP-91 protein was determined to be identical to AP-77, haptoglobin-alpha.

Figure 7A:
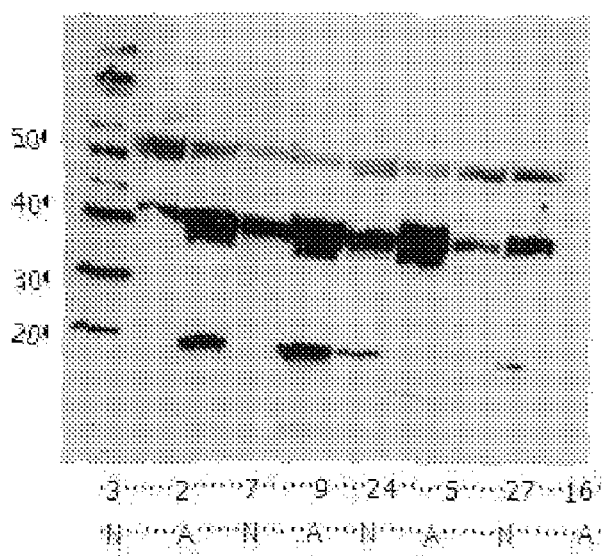
FIG. 7: Haptoglobin distribution. Haptoglobin western blot analysis of normal (N) and diseased (A) tissue. The numbers are sample ID numbers. Molecular weights are shown in kilodaltons. The alpha and beta subunits are >20 kd and 38 kd, respectively.
Figure 7B:
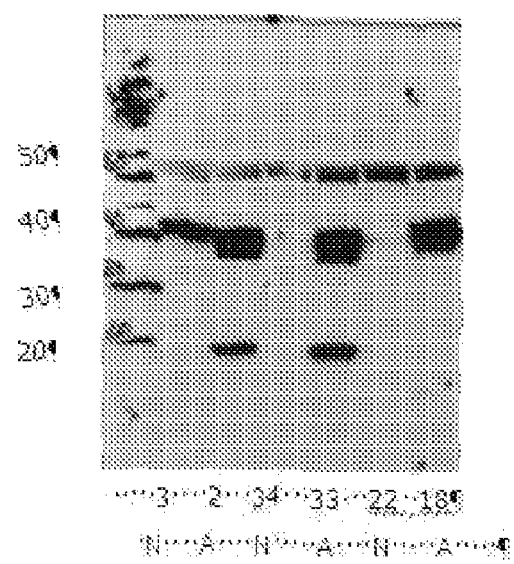

Elevated haptoglobin in diseased appendix tissue. In order to confirm the presence of haptoglobin in diseased tissue, an anti-haptoglobin antibody was used in western blotting of tissue extracts from individual normal and diseased appendices. FIG. 7 shows the western blot data from 6 normal and 6 appendicitis samples. Nearly every sample contained some level of the 38 kd beta subunit, however, there appeared to be an elevated level in cases of appendicitis. A >20 kilodalton band is present in every appendicitis sample and absent from all of the normal tissue samples. This data confirms the proteomic screen data and shows that the protein is an indicator of diseased appendix tissue. The alpha subunit has higher specificity than the beta subunit.

Example 3

Method of Identifying Molecules Using Fluid Samples

In variations of this example, fluid samples can include whole blood, serum, or plasma. The samples are whole blood collected from human patients immediately prior to an appendectomy. The specimens are placed on ice and transported to the lab. The blood is then processed by centrifugation at 3000 rpm for 15 minutes. Plasma is then separated by pouring into another container Upon performing an appendectomy, a patient is classified as having appendicitis (AP) or non-appendicitis (NAP). The classification is based on clinical evaluation, pathology, or both as known in the art. For cases of appendicitis, the clinical condition is also characterized as either perforated or non-perforated.

The samples from AP patients are optionally pooled and divided into aliquots. Optionally, a pooled aliquot is treated so as to remove selected components such as antibodies and serum albumin. Similarly, the samples from NAP patients are optionally pooled and divided into aliquots with optional treatment to remove the same selected components. Preferably the AP samples and NAP samples are processed in a similar manner.

Next, the pooled aliquots of AP and NAP samples are each subjected to two-dimensional gel electrophoresis as known in the art. The results of each sample type are compared with respect to the presence, absence, and relative expression levels of proteins. Preferably, one detects a signal corresponding to a protein derived from an AP sample that is either absent or expressed at relatively lower levels in a NAP sample. Further characterization is performed for such an AP protein.

The further characterization can include partial amino acid sequencing, mass spectrometry, and other analytical techniques as known in the art. A full length clone of the gene corresponding to the partial amino acid sequence can be isolated and expressed as a recombinant protein. The recombinant protein can be used as an antigen for detection. Alternatively, a partial or complete recombinant protein can be used to induce or otherwise generate a specific antibody reagent, polyclonal or monoclonal. The antibody reagent is used in the detection of antigen in a patient so as to aid in appendicitis diagnosis. A combination of antigenic molecules can be employed in appendicitis diagnosis.

Example 4

Method of Identifying Molecules Using Tissue Samples

Tissue samples are collected from appendicitis (AP) and non-appendicitis (NAP) patients. Preferably the tissue is the appendix. The AP or NAP tissues samples are optionally pooled so as to generate an AP tissue pool or an NAP tissue pool. The AP and NAP tissue samples are each used as a source for isolation of total RNA and/or mRNA. Upon isolation, the AP-RNA and NAP-RNA are maintained separately and used for preparation of cDNA.

A subtraction library is created using techniques available in the art. A cDNA library is optionally amplified. The cDNA library is treated so as to remove undesirable constituents such as highly redundant species and species expressed both in diseased and normal samples. Examples of the techniques include those described by Bonaldo et al. (1996) and Deichmann M et al. (2001).

Upon generation of the subtraction library, one analyzes, isolates, and sequences selected clones corresponding to sequences differentially expressed in the disease condition. Using molecular biology techniques, one selects candidates for recombinant expression of a partial or complete protein. Such a protein is then used as an antigen for detection. Alternatively, a partial or complete recombinant protein can be used to induce or otherwise generate a specific antibody reagent, polyclonal or monoclonal. The antibody reagent is used in the detection of antigen in a patient so as to aid in appendicitis diagnosis. It is envisioned that a combination of antigenic molecules can be employed in appendicitis diagnosis

Example 5

Method of Appendicitis Diagnosis by Evaluation of Plasma Sample Viscosity

Whole blood is drawn from a suspected appendicitis patient immediately prior to appendectomy. The specimens are placed on ice and transported to the clinical lab. The blood is processed by centrifugation at 3000 rpm for 15 minutes followed by separation of plasma from the sample by pouring into another container.

During the step of pouring, the samples are evaluated with respect to viscosity. Increased viscosity is indicative of appendicitis. Approximately 80% of samples corresponding to appendicitis cases demonstrate increased viscosity, whereas approximately none to less than 5% of samples corresponding to non-appendicitis cases demonstrate increased viscosity. It is noted that the degree of increased viscosity can correlate with the severity of appendicitis.

Viscosity measurements can be conducted by visual observation or by using techniques known in the art. For example, a Coulter Harkness capillary viscometer can be used (Harkness J., 1963) or other techniques (Haidekker M A, et al., 2002).

The presence of increased viscosity in plasma may be used in combination with other diagnostic techniques, for example with one or more of the following: physical examination, complete blood count (CBC) with or without differential, urinalysis (UA), computed tomography (CT), abdominal ultrasonography, and laparoscopy.

All references throughout this application, for example publications, patents, and patent documents, are incorporated by reference herein in their entireties, as though individually incorporated by reference, to the extent each reference is at not inconsistent with the disclosure in this application.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof.

The invention has been described with reference to various specific and preferred embodiments and techniques. However, it should be understood that many variations and modifications may be made while remaining within the spirit and scope of the invention. It will be apparent to one of ordinary skill in the art that compositions, methods, devices, device elements, materials, procedures, techniques, and embodiments, and variations respectively thereof, other than those specifically described herein can be applied to the practice of the invention as broadly disclosed herein without resort to undue experimentation. All art-known functional equivalents are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example and not of limitation.

REFERENCES

Aadland E, Fagerhol M K. Faecal calprotectin: a marker of inflammation throughout the intestinal tract. Europ J Gastroenterol Hepatol 2002; 14:1

Ahlquist D A, Gilbert J A. Stool markers for colorectal screening: future considerations. Dig Dis 1996; 14(3):132-44.

Alic M. Is fecal calprotectin the next standard in inflammatory bowel disease activity tests?. [Letter] American Journal of Gastroenterology 1999; 94(11):3370-1.

Arnott I D R, Watts D, Ghosh S. Review article: is clinical remission the optimum therapeutic goal in the treatment of Crohn's disease? Aliment Pharmacol Ther 2002; 16:857.

Arredouani M S, Kasran A, Vanoirbeek J A, Berger F G, Baumann H, Ceuppens J L. 2005. Haptoglobin dampens endotoxin-induced inflammatory effects both in vitro and in vivo. Immunology. 114(2):263-71.

Berger D, Bolke E, Seidelmann M, Beger H G. Time-scale of interleukin-6, myeloid related proteins (MRP), C reactive protein (CRP), and endotoxin plasma levels during the postoperative acute phase reaction. Shock 1997; 7(6):422-6.

Berntzen H B, Endresen G K, Fagerhol M K, Spiechowicz J, Mowinckel P. Calprotectin (the L1 protein) during surgery in patients with rheumatoid arthritis. Scand J Clin Lab Invest 1991; 51(7):643-50.

Berntzen H B, Fagerhol M K, Ostensen M, Mowinckel P, Hoyeraal H M. The L1 protein as a new indicator of inflammatory activity in patients with juvenile rheumatoid arthritis. J Rheumatol 1991; 18(1):133-8.

Berntzen H B, Munthe E, Fagerhol M K. A longitudinal study of the leukocyte protein L1 as an indicator of disease activity in patients with rheumatoid arthritis. J Rheumatol 1989; 16(11):1416-20.

Berntzen H B, Munthe E, Fagerhol M K. The major leukocyte protein L1 as an indicator of inflammatory joint disease. Scand J Rheumatol 1988; Supp 76:251-6.

Berntzen H B, Olmez U, Fagerhol M K, Munthe E. The leukocyte protein L1 in plasma and synovial fluid from patients with rheumatoid arthritis and osteoarthritis. Scand J Rheumatol 1991; 20(2):74-82.

Berstad A, Arsland G, Folvik G. Relationship between intestinal permeability and calprotectin in gut lavage fluid. Scand J Gastroenterol 2000; 35(1):64-9.

Bjarnason I, Sherwood R. Fecal calprotectin: a significant step in the noninvasive assessment of intestinal inflammation. J Pediatr Gastroent Nutr 2001; 33:11.

Bjerke K, Halstensen T S, Jahnsen F, Pulford K, Brandtzaeg P. Distribution of macrophages and granulocytes expressing L1 protein (calprotectin) in human Peyer's patches compared with normal ileal lamina propria and mesenteric lymph nodes. Gut 1993; 34(10):1357-63.

Bogumil T, Rieckmann P, Kubuschok B, Felgenhauer K, Bruck W. Serum levels of macrophage-derived protein MRP-8/14 are elevated in active multiple sclerosis. Neuroscience Letters 1998; 247(2-3):195-7

Bonaldo M F et al., 1996. Normalization and subtraction: Two approaches to facilitate Gene discovery. Genome Res. 6:791-806.

Brandtzaeg P, Dale I, Fagerhol M K. Distribution of a formalin-resistant myelomonocytic antigen (L1) in human tissues. I. Comparison with other leukocyte markers by paired immunofluorescence and immunoenzyme staining. Am J Clin Pathol 1987; 87(6):681-99.

Brandtzaeg P, Dale I, Fagerhol M K. Distribution of a formalin-resistant myelomonocytic antigen (L1) in human tissues. II. Normal and aberrant occurrence in various epithelia. Am J Clin Pathol 1987; 87(6):700-7.

Brandtzaeg P, Dale I, Gabrielsen T O. The leucocyte protein L1 (calprotectin): usefulness as an immunohistochemical marker antigen and putative biological function. Histopathol 1992; 21(2):191-6.

Brun J G, Cuida M, Jacobsen H, Kloster R, Johannesen A C, Hoyeraal H M, Jonsson R. Sjögren's syndrome in inflammatory rheumatic diseases: analysis of the leukocyte protein calprotectin in plasma and saliva. Scand J Rheumatol 1994; 23(3):114-8.

Brun J G, Haga H J, Boe E, Kallay I, Lekven C, Berntzen H B, Fagerhol M K. Calprotectin in patients with rheumatoid arthritis: relation to clinical and laboratory variables of disease activity. J Rheumatol 1992; 19(6):859-62.

Brydon W G, Campbell S S, Anderson N A, Wilson R G, Ghosh S. Faecal calprotectin levels and colorectal neoplasia. Gut 2001; 48(4):579-80.

Bunn S K, Bisset W M, Main M J, Golden B E. Fecal calprotectin as a measure of disease activity in childhood inflammatory bowel disease. J Pediatr Gastroenterol Nutr 2001; 32(2):171-7

Bunn S K, Bisset W M, Main M J C, Gray E S, Olson S, Golden B E. Fecal calprotectin: Validation as a noninvasive measure of bowel inflammation in childhood inflammatory bowel disease. J Pediatr Gastroenterol Nutr 2001; 33:11.

Burkhardt K, Radespiel-Troger M, Rupprecht H D, Goppelt-Struebe M, Riess R, Renders L, Hauser I A, and U Kunzendorf 2001. An increase in myeloid-related protein serum levels precedes acute renal allograft rejection. J Am Soc Nephrol 12:1947-57.

Clark B R, Kelly S E, Fleming S. Calgranulin expression and association with the keratinocyte cytoskeleton. J Pathol 1990; 160(1):25-30

Dale I, Brandtzaeg P, Fagerhol M K, Scott H. Distribution of a new myelomonocytic antigen (L1) in human peripheral blood leukocytes. Immunofluorescence and immunoperoxidase staining features in comparison with lysozyme and lactoferrin. Am J Clin Pathol 1985; 84(1):24-34.

Dale I, Brandtzaeg P. Expression of the epithelial L1 antigen as an immunohistochemical marker of squamous cell carcinoma of the lung. Histopathol 1989; 14(5):493-502.

Dale I. Plasma levels of the calcium-binding L1 leukocyte protein: standardization of blood collection and evaluation of reference intervals in healthy controls. Scand J Clin Lab Invest 1990; 50(8):837-41.

Deichmann, M., Polychronidis, M., Wacker, J., Thome, M. & Naher, H., 2001. The protein phosphatase 2A subunit Bg gene is identified to be differentially expressed in malignant melanomas by subtractive suppression hybridization. Melanoma Research 2001(11):1-9.

Dobryszycka W. 1997. Biological functions of haptoglobin—new pieces to an old puzzle. Eur J Clin Chem Clin Biochem 35(9):647-54.

Eversole L R, Miyasaki K T, Christensen R E. Keratinocyte expression of calprotectin in oral inflammatory mucosal diseases. J Oral Pathol Med 1993; 22(7):303-7.

Eversole L R, Miyasaki K T, Christensen R E. The distribution of the antimicrobial protein, calprotectin, in normal oral keratinocytes. Arch Oral Biol 1992; 37(11):963-8.

Fagerhol M K, Andersson K B, Naess-Andresen C F, Brandtzaeg P, Dale I. Calprotectin (The L1 Leukocyte Protein) In: V L Smith & J R Dedman (Eds): Stimulus Response Coupling. The Role of Intracellular Calcium-Binding Proteins, CRC Press, Boca Raton, Fla., USA, 1990, pp. 187-210.

Fagerhol M K. Calprotectin, a faecal marker of organic gastrointestinal abnormality. Lancet 2000; 356(9244):1783-4.

Flum D R et al., 2001. Has misdiagnosis of appendicitis decreased over time? A population-based analysis. JAMA 286 (14):1748-1753.

Fosse E, Moen O. Johnson E, Semb G, Brockmeier V, Mollnes T E, Fagerhol M K, Venge P. Reduced complement and granulocyte activation with heparin-coated cardiopulmonary bypass. Annals of Thoracic Surgery 1994; 58(2):472-7.

Frosch M, Strey A, Vogl T, Wulffraat N M, Kuis W, Sunderkotter C, Harms E, Sorg C, and J Roth 2000. Myeloid-related proteins 8 and 14 are specifically secreted during interaction of phagocytes and activated endothelium and are useful markers for monitoring disease activity in pauciarticular-onset juvenile rheumatoid arthritis. Arthritis Rheum 43:628-37.

Gabrielsen T O, Brandtzaeg P, Hoel P S, Dale I. Epithelial distribution of a myelomonocytic antigen L1 in relation to cutaneous malignancies and melanocytic naevi. Br J Dermatol 1988; 118(1):59-67.

Gabrielsen T O, Dale I, Brandtzaeg P, Hoel P S, Fagerhol M K, Larsen T E, Thune P O. Epidermal and dermal distribution of a myelomonocytic antigen (L1) shared by epithelial cells in various inflammatory skin diseases. J Am Acad Dermatol 1986; 15(2 Pt 1):173-9.

Garred P, Fosse E, Fagerhol M K, Videm V, Mollnes T E. Calprotectin and complement activation during major operations with or without cardiopulmonary bypass. Annals of Thoracic Surgery 1993; 55(3):694-9.

Gasché, C., 2005. Laboratory Tests—What Do They Tell Us?, Falk Symposium Abstract, Jun. 17-18, 2005, Munich, Germany.

Gaya D R, Mackenzie J F. Faecal calprotectin: a bright future for assessing disease activity in Crohn's disease. Q J Med 2002; 95:557 (editorial).

Gilbert J A, Ahlquist D A, Mahoney D W, Zinsmeister A R, Rubin J, Ellefson R D. Fecal marker variability in colorectal cancer: calprotectin versus hemoglobin. Scand J Gastroenterol 1996; 31(10):1001-5.

Golden B E, Clohessy P A, Russell G, Fagerhol M K. Calprotectin as a marker of inflammation in cystic fibrosis. Archives of Disease in Childhood 1996; 74(2):136-9.

Haga H J, Brun J G, Berntzen H B, Cervera R, Khamashta M, Hughes G R. Calprotectin in patients with systemic lupus erythematosus: relation to clinical and laboratory parameters of disease activity. Lupus 1993; 2(1):47-50.

Haidekker M A, et al., 2002. A novel approach to blood plasma viscosity measurement using fluorescent molecular rotors. Am J Physiol Heart Circ Physio 282:H1609-H1614.

Hammer H B, Kvien T K, Glennas A, Melby K. A longitudinal study of calprotectin as an inflammatory marker in patients with reactive arthritis. Clin Exp Rheumatol 1995; 13(1):59-64.

Hanai H, Takeuchi K, Iida T. Arai H, Kanaoka K, Iwasaki T. Nakamura A, Hosoda Y, Shirai N, Hirasawa K, Takahira K, Kataoka H, Sano M, Osawa M, Sugimoto S. Clinical significance of faecal calprotectin levels in patients with ulcerative colitis. Nippon Shokakibyo Gakkai Zasshi 2003; 100:21.

Harkness J., 1963. A new method for the measurement of plasma viscosity. Lancet 2:280-281.

Hetland G, Berntzen H B, Fagerhol M K. Levels of calprotectin (leukocyte L1 protein) during apheresis. Scand J Clin Lab Invest 1992; 52(6):479-82.

Homann C, Garred P, Graudal N, Hasselqvist P, Christiansen M, Fagerhol M K, Thomsen A C. Plasma calprotectin: a new prognostic marker of survival in alcohol-induced cirrhosis. Hepatol 1995; 21(4):979-85.

Hsieh H L, Schafer B W, Weigle B, and C W Heizmann 2004 S100 protein translocation in response to extracellular S100 is mediated by receptor for advanced glycation endproducts in human endothelial cells. Biochem Biophys Res Commun 316:949-59.

Hycult Biotechnology b.v., ELISA Test Kit for Human Calprotectin information sheet, Catalog No. HK325.

Hycult Biotechnology b.v., Monoclonal Antibody to Human S100A8/A9 (MRP-8/MRP-14), calprotectin Clone 27E10 information sheet, Catalog No. HM2156.

Ikemoto, M., et al. 2003. New ELISA System for Myeloid-related Protein Complex (MRP8/14) and its Clinical Significance as a Sensitive Marker for Inflammatory Responses Associated with Transplant Rejection, Clin. Chem. 49:594-600.

Johne B, Fagerhol M K, Lyberg T, Prydz H, Brandtzaeg P, Naess-Andresen CF, Dale I. Functional and clinical aspects of the myelomonocyte protein calprotectin. Molecular Pathology 1997; 50(3):113-23.

Johne B, Kronborg O, Ton H I, Kristinsson J, Fuglerud P. A new fecal calprotectin test for colorectal neoplasia. Clinical results and comparison with previous method. Scand J Gastroenterol 2001; 36(3):291-6.

Katnik et al, 1989. Monoclonal Antibodies Against Human Haptoglobin. Hybridoma 8:(5):551-560.

Kelly S E, Hunter J A, Jones D B, Clark B R, Fleming S. Morphological evidence for calcium-dependent association of calgranulin with the epidermal cytoskeleton in inflammatory dermatoses. Br J Dermatol 1991; 124(5):403-9.

Kelly S E, Jones D B, Fleming S. Calgranulin expression in inflammatory dermatoses. J Pathol 1989; 159(1):17-21.

Kerkhoff C, Klempt M, Sorg C. Novel insights into structure and function of MRP8 (S100A8) and MRP14 (S100A9). Biochimica et Biophysica Acta 1998; 1448(2):200-11.

Kjeldsen-Kragh J, Mellbye O J, Haugen M, Mollnes T E, Hammer H B, Sioud M, Forre O. Changes in laboratory variables in rheumatoid arthritis patients during a trial of fasting and one-year vegetarian diet. Scand J Rheumatol 1995; 24(2):85-93.

Koike T. Kondo K, Makita T. Kajiyama K, Yoshida T. Morikawa M. Intracellular localization of migration inhibitory factor-related protein (MRP) and detection of cell surface MRP binding sites on human leukemia cell lines. J Biochem 1998; 123(6):1079-87.

Kristinsson J, Armbruster C H, Ugstad M, Kriwanek S, Nygaard K, Ton H, Fuglerud P. Fecal excretion of calprotectin in colorectal cancer; relationship to tumor characteristics. Scand J Gastroenterol 2001; 36(2):202-7.

Kristinsson J, Roseth A, Fagerhol M K, Aadland E, Schjonsby H, Bormer O P, Raknerud N, Nygaard K. Fecal calprotectin concentration in patients with colorectal carcinoma. Diseases of the Colon & Rectum 1998; 41 (3):316-21.

Kronborg O, Ugstad M, Fuglerud P, Johne B, Hardcastle J, Scholefield J H, Vellacott K, Moshakis V, Reynolds J R. Faecal calprotectin levels in a high risk population for colorectal neoplasia. Gut 2000; 46(6):795-800.

Kumar, R. K., et al. 2001. Dimeric S100A8 in human neutrophils is diminished after phagocytosis, J. Leukoc. Biol. 70(1):59-64.

Limburg P J, Ahlquist D A, Sandborn W J, Mahoney D W, Devens M E, Harrington J J and A R Zinsmeister 2000. Fecal calprotectin levels predict colorectal inflammation among patients with chronic diarrhea referred for colonoscopy. Am J Gastroenterol, 10:2831-7.

Limburg P J. Ahlquist D A. Sandborn W J. Mahoney D W. Devens M E. Harrington J J. Zinsmeister A R. Fecal calprotectin levels predict colorectal inflammation among patients with chronic diarrhea referred for colonoscopy. American Journal of Gastroenterology 2000; 95(10):2831-7.

Longbottom D, Sallenave J M, van Heyningen V. Subunit structure of calgranulins A and B obtained from sputum, plasma, granulocytes and cultured epithelial cells. Biochimica et Biophysica Acta 1992; 1120(2):215-22.

Lugering N, Stoll R, Schmid K W, Kucharzik T. Stein H, Burmeister G, Sorg C, Domschke W. The myeloic related protein MRP8/14 (27E10 antigen)-usefulness as a potential marker for disease activity in ulcerative colitis and putative biological function. Europ J Clin Invest 1995; 25(9):659-64.

Meling T R. Aabakken L. Roseth A. Osnes M. Faecal calprotectin shedding after short-term treatment with non-steroidal anti-inflammatory drugs. Scandinavian Journal of Gastroenterology 1996; 31 (4):339-44.

Moen O, Fosse E, Braten J, Andersson C, Fagerhol M K, Venge P, Hogasen K, Mollnes T E. Roller and centrifugal pumps compared in vitro with regard to haemolysis, granulocyte and complement activation. Perfusion 1994; 9(2):109-17.

Muller F, Froland S S, Aukrust P, Fagerhol M K. Elevated serum calprotectin levels in HIV-infected patients: the calprotectin response during ZDV treatment is associated with clinical events. J Acq Immune Defic Syndr 1994; 7(9):931-9.

Muller, F., et al. 1994. Elevated serum calprotectin levels in HIV-infected patients: the calprotectin response during ZDV treatment is associated with clinical events, J. Acqui. Immune Defic. Syndr. 7(9):931-939.

Neary, Walter, 2001. Press Release from University of Washington, Misdiagnosis of appendicitis continues despite new tools.

Olafsdottir E, Aksnes L, Fluge G, Berstad A. Faecal calprotectin in infants with infantile colic, healthy infants, children with inflammatory bowel disease, children with recurrent abdominal pain and healthy children. Acta Paediatr 2002; 91:45.

Pekna M, Borowiec J, Fagerhol M K, Venge P, Thelin S. Biocompatibility of heparin-coated circuits used in cardiopulmonary bypass. Scand J Thorac Cardiovasc Surg 1994; 28(1):5-11.

Power, C. et al, 2005. Raised faecal calprotectin levels in patients presenting with right iliac fossa pain warrant mandatory laparoscopy: a non-invasive predictor of acute appendicitis, Thieme connect, Endoscopy 37:DOI1:10.1055/2-2005-868524.

Power, C., et al. 2004, Irish Society of Gastroenterology Winter Meeting Program Oral Presentation Raised Faecal Calprotectin Levels in Patients Presenting with Right Iliac Fossa Pain Warrant Mandatory Laparoscopy: A Non-invasive Predictor of Acute Appendicitis.

Robinson M J, Tessier P, Poulsom R, and N. Hogg 2002 The S100 family heterodimer, MRP-8/14, binds with high affinity to heparin and heparan sulfate glycosaminoglycans on endothelial cells. J Biol Chem. 277:3658-65.

Roseth A G, Aadland E, Grzyb K. Normalization of faecal calprotectin: a predictor of mucosal healing in patients with inflammatory bowel disease. Scand J. Gastroenterol. 2004 October; 39(10):1017-20.

Roseth A G, Fagerhol M K, Aadland E, Schjonsby H. Assessment of the neutrophil dominating protein calprotectin in feces. A methodologic study. Scand J Gastroenterol 1992; 27(9):793-8.

Roseth A G, Kristinsson J, Fagerhol M K, Schjonsby H, Aadland E, Nygaard K, Roald B. Faecal calprotectin: a novel test for the diagnosis of colorectal cancer? Scand J Gastroenterol 1993; 28(12):1073-6.

Roseth A G. Aadland E. Jahnsen J. Raknerud N. Assessment of disease activity in ulcerative colitis by faecal calprotectin, a novel granulocyte marker protein. Digestion 1997; 58(2):176-80.

Roseth A G. Fagerhol M K. Aadland E. Schjonsby H. Assessment of the neutrophil dominating protein calprotectin in feces. A methodologic study. Scandinavian Journal of Gastroenterology 1992; 27(9):793-8.

Roseth A G. Schmidt P N. Fagerhol M K. Correlation between faecal excretion of indium-111-labelled granulocytes and calprotectin, a granulocyte marker protein, in patients with inflammatory bowel disease. Scandinavian Journal of Gastroenterology 1999; 34(1):50-4.

Ryckman C, Vandal K, Rouleau P, Talbot M, and P A Tessier 2003 Proinflammatory activities of S100: proteins S100A8, S100A9, and S100A8/A9 induce neutrophil chemotaxis and adhesion. J. Immunol. 170:3233-42.

Saintigny G, Schmidt R, Shroot B, Juhlin L, Reichert U, Michel S. Differential expression of calgranulin A and B in various epithelial cell lines and reconstructed epidermis. J Invest Dermatol 1992; 99(5):639-44.

Sander J, Fagerhol M K, Bakken J S, Dale I. Plasma levels of the leucocyte L1 protein in febrile conditions: relation to aetiology, number of leucocytes in blood, blood sedimentation reaction and C-reactive protein. Scand J Clin Lab Invest 1984; 44(4):357-62.

Semb A G, Gabrielsen T O, Halstensen T S, Fagerhol M K, Brandtzaeg P, Vaage J. Cardiac surgery and distribution of the leukocyte L1 protein-calprotectin. Europ J Cardio-Thoracic Surgery 1991; 5(7):363-7.

Shanahan F. Inflammatory bowel disease: immunodiagnostics, immunotherapeutics, and ecotherapeutics. Gastroenterol 2001; 120:622.

Stockley R A, Dale I, Hill S L, Fagerhol M K. Relationship of neutrophil cytoplasmic protein (L1) to acute and chronic lung disease. Scand J Clin Lab Invest 1984; 44(7):629-34.

Striz, I. and I. Trebichavsky 2004. Calprotectin—a Pleiotropic Molecule in Acute and Chronic Inflammation. Physiol Res. 53:245-253.

Thomas P. Rihani H. Roseth A. Sigthorsson G. Price A. Nicholls R J. Bjarnason I. Assessment of ileal pouch inflammation by single-stool calprotectin assay. Diseases of the Colon & Rectum 2000; 43(2):214-20.

Tibble J, Sigthorsson G, Foster R, Fagerhol M K, Bjarnason I. Faecal calprotectin and faecal occult blood tests in the diagnosis of colorectal carcinoma and adenoma. Gut 2001; 49:402.

Tibble J. Teahon K. Thjodleifsson B. Roseth A. Sigthorsson G. Bridger S. Foster R. Sherwood R. Fagerhol M. Bjarnason I. A simple method for assessing intestinal inflammation in Crohn's disease. Gut 2000; 47(4):506-13.

Tibble J A, Bjarnason I. Department of Medicine, Guy's, King's, St Thomas's Medical School, Bessemer Road, London SE5 9PJ, UK. Non-invasive investigation of flammatory bowel disease.

Tibble J A, Bjarnason I. Department of Medicine, Guy's, King's, St. Thomas's Medical School, London, UK. Fecal-calprotectin as an index of intestinal inflammation.

Tibble J A, Bjarnason I. Markers of intestinal inflammation and predictors of clinical relapse in patients with quiescent IBD. Medscape Gastroenterol 2001; 3 (2).

Tibble J A. Sigthorsson G. Bridger S. Fagerhol M K. Bjarnason I. Surrogate markers of intestinal inflammation are predictive of relapse in patients with inflammatory bowel disease. [Journal Article] Gastroenterology 2000; 119(1):15-22.

Tibble J A. Sigthorsson G. Foster R. Scott D. Fagerhol M K. Roseth A. Bjarnason I. High prevalence of NSAID enteropathy as shown by a simple faecal test. Gut 1999; 45(3):362-6.

Ton H. Brandsnes. Dale S. Holtlund J. Skuibina E. Schjonsby H. Johne B. Improved assay for fecal calprotectin. Clinica Chimica Acta 2000; 292(1-2):41-54.

Tungekar M F, Heryet A, Gatter K C. The L1 antigen and squamous metaplasia in the bladder. Histopathol 1991; 19(3): 245-50.

U.S. Pat. No. 5,350,687, Odink, et al., Sep. 27, 1994, Antibodies which bind to novel lymphokine related peptides.

U.S. Pat. No. 5,455,160, Fagerhol, et al., Diagnostic test and kit for disease disorders in the digestive system.

U.S. Pat. No. 5,552,295, Stanker, et al., Sep. 3, 1996, Monoclonal antibodies to bovine haptoglobin and methods for detecting serum haptoglobin levels.

U.S. Pat. No. 6,451,550, Eckersall, Sep. 17, 2002, Haptoglobin assay.

U.S. Patent Publication No. 20030224452, Colgin, et al., Pregnancy Detection.

Wilkinson M M, Busuttil A, Hayward C, Brock D J, Dorin J R, Van Heyningen V. Expression pattern of two related cystic fibrosis-associated calcium-binding proteins in normal and abnormal tissues. J Cell Science 1988; 91 (Pt 2):221-30.

Ye B, Cramer D W, Skates S J, Gygi S P, Pratomo V, Fu L, Horick N K, Licklider L J, Schorge J O, Berkowitz R S, Mok S C. 2003 Haptoglobin-alpha subunit as potential serum biomarker in ovarian cancer: identification and characterization using proteomic profiling and mass spectrometry. Clin Cancer Res 9(8):2904-11.

Yerly S, Bouvier M, Rougemont A, Srivastava I, Perrin L H. 1990. Development of a haptoglobin ELISA. Its use as an indicator for malaria. Acta Trop. 1990 47(4):237-44.

The invention claimed is:

1. An immunoassay test device for detecting the presence of a level of MRP-8/14 that is differentially associated with appendicitis in a sample of blood, plasma or serum from a patient suspected of having appendicitis, said device comprising:
 a first antibody specific to MRP-8/14;
 a support for said first antibody;
 an indictor for detecting binding of said first antibody with said MRP-8/14 when said antibody is in contact with a sample containing said MRP-8/14, said sample being blood, serum or plasma of said patient, wherein said patient is not known to have an interfering condition associated with the presence of elevated MRP-8/14 protein in blood, serum or plasma of said patient, said interfering condition being selected from the group consisting of recent allograft; septicaemia; meningitis; pneumonia; tuberculosis; rheumatoid arthritis; gastrointestinal cancer; inflammatory bowel disease; skin cancer, periodontitis, preeclampsia, and AIDS;
 wherein said immunoassay device is capable of detecting a level of MRP-8/14 in said sample higher than 10 micrograms per ml.

2. A device according to claim 1, wherein said first antibody is 27e10.

3. A device according to claim 1 also comprising a second antibody, said second antibody being to haptoglobin, to test for the presence of haptoglobin in said sample.

4. A device according to claim 1, also comprising means for lysing cells in said sample.

5. The immunoassay test device of claim 1, which is a lateral flow device comprising inlet means for flowing a liquid sample into contact with said first antibody.

6. The immunoassay test device of claim 5 also comprising a filter for filtering serum or plasma from a blood sample.

7. The immunoassay test device of claim 1 also comprising a housing.

8. The immunoassay test device of claim 1 in the format of a dipstick or a cartridge.

9. A kit comprising the device of claim 1 and instructions for using said device.

10. The immunoassay test device of claim 1 also comprising a masking component for detecting a level of MRP-8/14 in said sample higher than 10 micrograms per ml.

11. The immunoassay test device of claim 1 also comprising said sample.

12. The immunoassay test device of claim 1 in which the patient suspected of having appendicitis shows a symptom selected from the group consisting of: abdominal discomfort or abdominal pain or periumbilical pain; pain that starts near the navel, then moves to the lower right quadrant of the abdomen; anorexia, trouble eating accompanied by sleepiness; nausea starting after onset of said abdominal or periumbilical pain; vomiting starting after onset of abdominal or periumbilical pain; vomiting accompanied by fatigue; constipation; small stools with mucus; diarrhea; inability to pass gas; low-grade fever; abdominal swelling; pain in abdomen worsening; tenesmus; and high fever.

* * * * *